United States Patent [19]

Wasson et al.

[11] 3,944,560

[45] Mar. 16, 1976

[54] 3-HYDROXY-3-(1,2,5-THIADIAZOLYLOXYALKANOL)-3,4-DIHYDRO-2H-1,5-BENZODIOXEPIN PRODUCTS

[75] Inventors: Burton K. Wasson, Valois; Haydn W. R. Williams, Dollard des Ormeaux, both of Canada

[73] Assignee: Merck & Co., Inc., Rahway, N.J.

[22] Filed: Nov. 21, 1973

[21] Appl. No.: 417,868

Related U.S. Application Data

[60] Division of Ser. No. 249,422, May 1, 1972, Pat. No. 3,812,150, which is a division of Ser. No. 832,879, June 9, 1969, Pat. No. 3,700,691, which is a continuation-in-part of Ser. No. 755,442, Aug. 26, 1968, abandoned.

[52] U.S. Cl. ............................................. 260/302 H
[51] Int. Cl.² ........................................ C07D 285/10
[58] Field of Search ............................... 260/302 H

[56] References Cited
UNITED STATES PATENTS
3,655,663   4/1972   Wasson........................... 260/302 D

*Primary Examiner*—R. Gallagher
*Attorney, Agent, or Firm*—David L. Rose; Edmunde D. Riedl; J. Jerome Behan

[57] ABSTRACT

3-Hydroxy-3-(substituted-aminoalkyl-3,4-dihydro-2H-1,5-benzodioxepin products are described that exhibit -advenergic stimulating properties and are therefore suitable for use as bronchodilating agents. The products are prepared essentially by four principal routes from 3-oxo-3,4-dihydro-2H-1,5-benzodioxepins. By one route the 3-oxobenzodioxepin is treated with a nitroalkane to give a 3-hydroxy-3-nitroalkyl-benzodioxepin the nitro group of which is reduced to an amine and the resulting compound reacted with an aldehyde or ketone under hydrogenating conditions to introduce the desired substituent into the amino function. By a second route the 3-oxobenzodioxepin is reacted with an alkali metal nitrile to form the cyanhydrin which upon reduction forms the 3-hydroxy-3-aminoalkyl-benzodioxepin that can be treated with a ketone or aldehyde to give the desired products or can be reacted with sodium nitrite or other agent to form a 3-spiro-benzodioxepin-2-oxirane which upon reaction with an amine provides the desired product. The 3-spiro-benzodioxepin-2′-oxirane also can be obtained by treatment of the 3-oxo-benzodioxepin with a sulfurylide, A fourth method involves forming a benzodioxepin-3-spiro-5′-oxazolidin-2′-one which upon treatment with dilute alkali gives the desired 3-hydroxy-3-(substituted aminoalkyl)-3,4-dihydro-2H-1,5-benzodioxepin The intermediate oxazolidinone compounds can be treated if desired with various agents to attach substituents on the benzenoid moiety of the starting substance. These oxazolidinones exhibit β-stimulating and skeletal muscle relaxant properties.

5 Claims, No Drawings

3-HYDROXY-3-(1,2,5-THIADIAZOLYLOXYALKANOL)-3,4-DIHYDRO-2H-1,5-BENZODIOXEPIN PRODUCTS

RELATIONSHIP TO OTHER APPLICATIONS

This application is a division of application Ser. No. 249,422 filed May 1, 1972 now U.S. Pat. No. 3,812,150 issued May 21, 1974 which in turn is a division of the then copending application Ser. No. 832,879 filed June 9, 1969 now U.S. Pat. No. 3,700,691 issued Oct. 24, 1972 which in turn is a continuation in-part of the then copending application Ser. No. 755,442 filed Aug. 26, 1968 now abandoned.

This invention is concerned with 3,3-disubstituted benzodioxepins which exhibit β-aurenergic stimulating properties which make them uniquely suitable for use as broncho-dilating agents.

The novel 3,3-disubstituted benzodioxepins of this invention can be illustrated by the structural formula

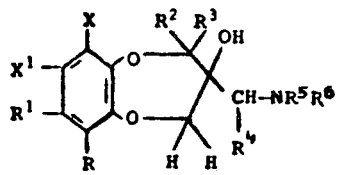

and pharmacologically acceptable salts thereof wherein R is selected from hydrogen, hydroxy, lower alkyl ($C_{1-5}$) and lower alkoxy ($C_{1-3}$); $R^1$ is selected from hydrogen, halogen particularly chloro and bromo, lower alkyl ($C_{1-5}$), nitro, amino, mono- or di-lower alkylamino, acylamino wherein the acyl radical is the residue of an alkyl ($C_{1-3}$) sulfonic acid or an alkyl ($C_{1-3}$) carboxylic acid, lower carboalkoxyamino, hydroxy or lower alkoxy ($C_{1-5}$); X and $X^1$ are selected from hydrogen, lower alkyl ($C_{1-5}$) and halogen; $R_2$ and $R_3$ can be the same or dissimilar and are each separately selected from hydrogen, lower alkyl ($C_{1-5}$), phenyl or phenyl-lower alkyl ($C_{1-3}$), lower cycloalkyl, pyridyl and pyridyl-lower alkyl ($C_{1-3}$); $R^4$ is selected from hydrogen and lower alkyl ($C_{1-5}$), and the grouping $-NR^5R^6$ represents the amino group or a mono- or disubstituted amino group or a nitrogen containing heterocyclic group and in particular an $-NR^5R^6$ group where $R^5$ represents hydrogen, lower alkyl ($C_{1-5}$), and substituted lower alkyl such as 2-phenyl-2-hydroxyethyl, and $R^6$ represents (1) lower alkyl having advantageously from 1 to 10 carbon atoms and being either straight or branched chain, and being either unsubstituted or substituted with one or more groups selected from (a) amino or mono- or di-loweralkyl ($C_{1-5}$) amino, or the amino substituent can be

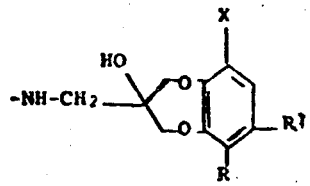

wherein R, $R^1$ and X have the above assigned meanings, (b) cycloalkyl having from 3 to 6 carbon atoms, (c) lower alkoxy having from 1 to 3 carbon atoms, (d) hydroxy substituted lower alkoxy having from 1 to 3 carbon atoms, (e) hydroxy, (f) phenyl or mono- or poly-substituted phenyl wherein the substituents are selected from halo especially chloro or bromo, hydroxy and lower alkoxy ($C_{1-3}$) or wherein the substituted phenyl is the 3,4-methylenedioxyphenyl, (g) a heterocyclic substituent such as an indelyl, morpholino or 1,2,5-thiadiazolyloxy, (2) a cycloaliphatic such as a cycloalkyl having from 3 to 10 carbon atoms such as cyclopropyl, cyclobutyl, cyclopentyl, cyclohexyl, tricyclodecane such as adamantyl and the like, or a phenyl-lowercycloalkyl as phenyl-cyclohexyl, (3) lower alkenyl having from 3 to 5 carbon atoms, (4) lower alkynyl having from 3 to 5 carbon atoms, (5) phenyl or substituted phenyl wherein the mono- or poly-substituents are selected from a halogen such as chloro and bromo, lower alkyl ($C_{1-3}$) and lower alkoxy ($C_{1-3}$), (6) a heterocyclic substituent such as 2-pyridyl, (7) the residue of a guanidine moiety of the structure

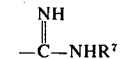

wherein $R^7$ is hydrogen, lower alkyl, benzyl or phenyl or substituted phenyl wherein the substituent is one or more groups selected from halo, especially chloro or bromo, lower alkyl ($C_{1-3}$), or lower alkoxy ($C_{1-3}$) (8) the benzodioxepin radical

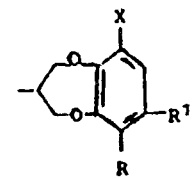

wherein R, $R^1$ and X have the above assigned meanings, but preferably they represent hydrogen; and in addition the grouping $-NR^5R^6$ can represent a morpholino, piperazinyl, N-phenylpiperazinyl, 1-aziridinyl or 3-(2-iminothiazolidinyl) group.

The novel 3,3-disubstituted benzodioxepins of this invention advantageously are prepared by the reactions illustrated in Flow Diagram I.

FLOW DIAGRAM I

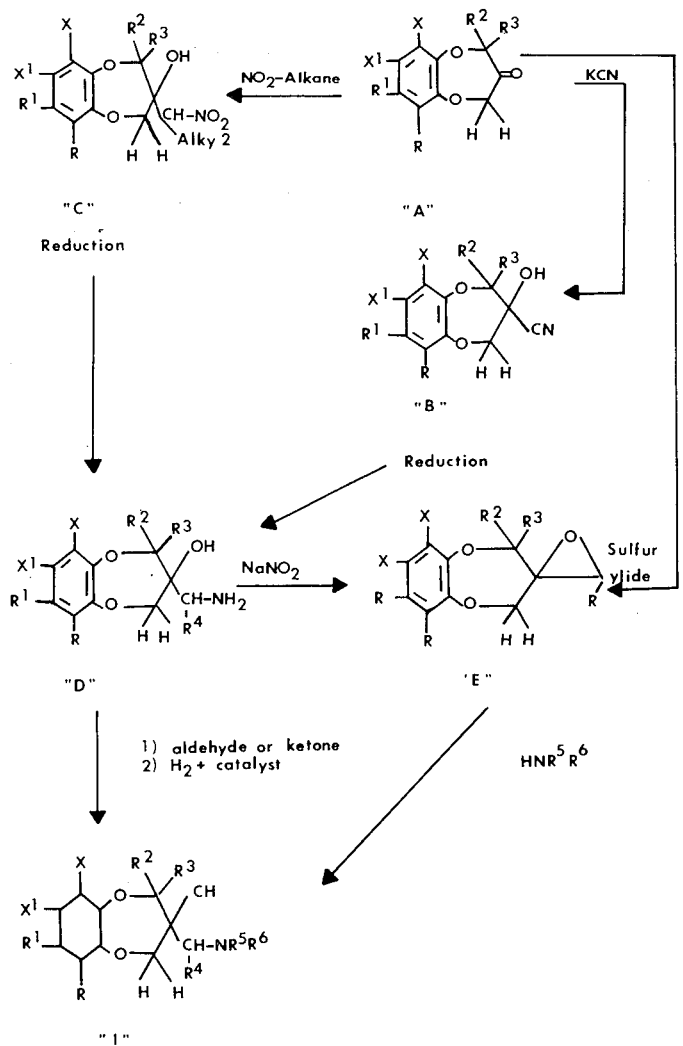

According to the above reaction scheme it is seen that the desired 3,4 dihydro-2H-1,5-benzodioxepin, product I, is obtained from the 3-keto compound A by one of two methods depending upon whether $R^4$ is hydrogen or whether it represents a lower alkyl group of from 1 to 4 carbons. Additionally, the 3-keto compound A can be directly converted to the 3-spiro-2'-oxirane E by use of a sulfur ylide.

When $R^4$ is hydrogen, the 3-keto intermediate A in an acidic solvent is caused to react with aqueous hydrogen cyanide, conveniently generated in situ from sodium or potassium cyanide to provide the 3-hydroxy-3-cyano intermediate C which is separated and reduced to provide the 3-hydroxy-3-aminoalkyl intermediate D. Treatment of intermediate D with acetone or other ketone of aldehyde that will yield the group $R^6$ upon reduction provides the desired product I. Intermediate "D" also can be treated with an alkali nitrite to form the 3-spiro-2'-oxirane E which when reacted with the desired amine forms product I.

The first step of the above procedure, that is treatment of the 3-keto compound A with aqueous alkali cyanide, advantageously is carried out in the presence of acetic anhydride or other acidic solvent, e.g., acetic acid or alternatively with anhydrous hydrogen cyanide. The reduction of intermediate C can be either a catalytic or chemical reduction; catalytic reduction preferably being carried out with a transition metal catalyst such as platinum, palladium, nickel, ruthenium, rhodium and the like in a mixture of a lower alkanol ($C_{1-4}$) and acetic acid supplemented if necessary with a trace of mineral acid, i.e. hydrochloric acid, or if desired chemical reduction can be effected with a metal hydride advantageously lithium aluminum hydride or other metal hydrides, preferably in diethyl ether or tetrahydrofuran. Each method affords good yields of product D.

Intermediate D then can be converted to the desired 3,3-disubstituted benzodioxepin "I" of this invention by either of two routes. One of the routes employed for preparing product "I" wherein $R^5$ is hydrogen, involves the reaction of intermediate D with a ketone or aldehyde that will yield the group $R^6$ and subsequent reduction advantageously carried out by hydrogenation in the presence of a transition metal catalyst in an organic solvent such as a lower alkanol as ethanol, propanol, butanol or isomers thereof and the like, employing acidic conditions when required or chemical reduction with sodium borohydride can be employed.

The second more general method for preparing product I where $R^5$ and $R^6$ have the meaning given above involves the reaction of intermediate D with an alkyl nitrite or with nitrous acid generated in situ from an alkali metal nitrite (sodium or potassium nitrite being quite suitable) advantageously carried out in an aqueous medium in the presence of an organic acid, acetic acid being preferred, and advantageously with cooling to provide a 3-spiro-2'-oxirane E as well as the 3-hydroxy-3-hydroxymethyl analog. The novel 3-hydroxy-3-hydroxymethyl products also exhibit β-adrenergic stimulating properties, and constitute another feature of this invention. The 3-spiro-2'-oxirane E obtained then is reacted with the amine, $HNR^5R^6$, advantageously in the presence of an organic solvent such as a lower alkanol at ambient temperature to give the benzodioxepin I. When $R^5$ represents the amidine group,

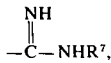

these products also can be prepared by reaction of product I wherein $R^5$ and $R^6$ represent hydrogen with an S-loweralkylisothiuronium salt of the structure

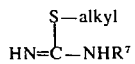

advantageously with heating up to about the reflux temperature of the reaction mixture. When $-NR^5R^6$ in product I is the 1-aziridinyl group treatment of said compound with sodium thiocyanate under acid conditions (pH no greater than 4) provides product I wherein $-NR^5R^6$ is the 3-(2-iminothiazolidinyl) group.

Product I wherein R, $R^1$, X and $R^5$ represent hydrogen can be employed as starting materials to prepare end products wherein R, $R^1$ and X are other than hydrogen and particularly where $R^1$ is nitro, amino, lower acylamino and hydroxy. These latter compounds can be prepared by the methods described above or by initially treating a 3-hydroxy-3-($R^6$NH-CH$_2$)-benzodioxepin with phosgene in the presence of a base. Phosgene advantageously in admixture with chloroform is added dropwise with stirring to a cooled solution of the benzodioxepin in the same solvent. The 3-spiro-5'-oxazolidin-2'-one obtained is admixed with acetic acid, cooled to the freezing point and treated dropwise with a mixture of nitric acid and sulfuric acid to provide the corresponding 7-nitro-3-spiro-5'-oxazolidin-2'-one compound which in the presence of dilute alkali, as aqueous sodium or potassium hydroxide, gives the desired 7-nitro-3-hydroxy-3-($R^6$NHCH$_2$-)benzodioxepin, I-a.

Catalytic reduction of I-a or its intermediate 7-nitro-3-spiro-5'-oxazolidin-2'-one, advantageously with palladium or Raney Nickel, provides the corresponding 7-amino derivative. The 7-amino-3-spiro-5'-oxazolidin-2'-one when treated with aqueous alkali gives the 7-amino-3-hydroxy-3-($R^6$NHCH$_2$—) benzodioxepin, I-b.

Product I-a also can be converted to the 7-amino analog, I-b, or to the 7-lower acylamino by first reacting I-a with an aldehyde YCHO, wherein Y can be lower alkyl, phenyl or the residue of any commercially available aliphatic or aromatic aldehyde, to form the 7-nitro-2'-Y-3-spiro-5'-oxazolidine which, upon reduction as described above, gives the corresponding 7-amino compound which can either be treated with aqueous alkali to provide product I-b or treated with a lower alkyl sulfonyl halide or a lower alkanoyl halide to give the corresponding 7-acylamino2'-Y-3-spiro-5'-oxazolidine which when treated with acid, especially with a mineral acid or strong organic acid, gives the 7-acylamino-3-hydroxy-3-($R^6$-NHCH$_2$—) benzodioxepin, I-c.

Diazotization of the 7-amino-3-spiro-5'-oxazolidin-2'-one, prepared as described above, gives the corresponding 7-hydroxy compound which, in the presence of base, such as barium hydroxide gives 3,7-dihydroxy-3-($R^6$NHCH$_2$)benzodioxepin, I-d.

The 6- and/or 7-hydroxy-benzodioxepins, I, also can be prepared from the corresponding 6- and/or 7-alkoxybenzodioxepins by treatment with strong mineral acid.

The 3-spiro-2'-oxirane E can also be prepared by treatment of the 3-keto compound A with either dimethylenesulfonium methylide or dimethylsulfonium methylide either with cooling or at a temperature up to ambient temperature. In practice, the dimethyloxosulfonium methylide is prepared under nitrogen from sodium hydride, trimethyloxosulfonium iodide and dimethyl sulfoxide. The ketone, A, is added slowly to the mixture at ambient temperature and the mixture stirred for about 24 hours. The dimethylsulfonium methylide advantageously is prepared from butyl lithium and trimethylsulfonium iodide in tetrahydrofuran. The ketone A then is added and the reaction mixture held at 0° C. for 1 hour and then for a short period at ambient temperature. Isolation in each instance provides the desired 3-spiro-2'-oxirane, E.

To prepare the products wherein $R^4$ is a lower alkyl group, the ketone A initially is reacted with a nitroalkane to give intermediate B which upon reduction provides intermediate D. The reaction of the ketone A with the nitro-alkane advantageously is carried out in ethanol or other lower alkanol or ether in the presence of sodium ethoxide or other alkali metal alkoxide to give a salt of B from which the compound is liberated by treatment with a weak acid such as acetic acid. The reduction of intermediate B to form D is effected advantageously in ethanol (or other lower alkanol)-acetic acid with hydrogen and Raney Nickel or palladium.

While the unsubstituted 3-keto compound A is known, it was obtained in low yields as a by-product in the preparation of 1,4-benzodioxane-3-carboxylic acid. All attempts by these investigators to prepare the 3-keto-benzodioxepin either failed or provided very small yields of the desired product. A process thus had to be devised for the preparation of this ketone which has been found to give very high yields of compound A. This novel synthetic route for the preparation of the 3-keto compound A can be illustrated as shown in Flow Diagram II.

FLOW DIAGRAM II

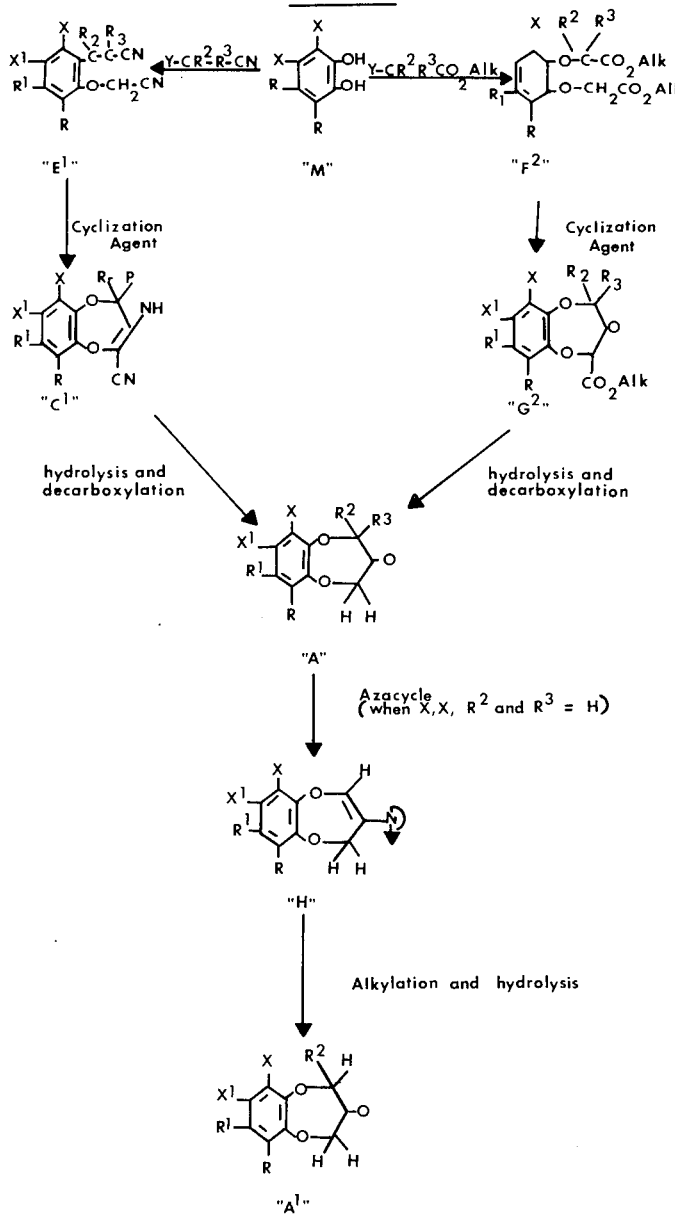

According to the reaction scheme illustrated in Flow Diagram II, the catechol starting material E is converted to the 3-keto product A by initial reaction with a haloalkanonitrile or a haloalkanoic acid ester.

Treatment of the catechol E with a haol-acetonitrile of the structure X-CR³R³-CN, to afford the 1,2 bis(-cyanoalkoxy)-benzene, "F¹" is carried out in one step when R² and R³ each represent hydrogen, however, when it is desired to form product "F¹" wherein R² and R³ are other than hydrogen, then the catechol (R=R¹=H) initially is treated with one equivalent of halo-acetonitrile, the ortho-cyanomethoxyphenol isolated and then reacted with the haloalkanonitrile to give F¹ wherein R² and/or R³ are other than hydrogen.

When R or R¹ is other than hydrogen then it is preferred to use the appropriately substituted salicylaldehyde which is treated with the appropriate haloalkanonitrile, and the resulting compound oxidized by peracetic acid followed by mild hydrolysis to give the orthocyanoalkoxyphenol which then is treated with haloacetonitrile to provide F¹. Product F¹ then is cyclized by treatment with a mixture of sodamide and a solvent selected preferably from dimethyl sulfoxide (DMSO), dimethylformamide (DMF), sulfolane, benzene, toluene or xylene or by treatment with an alkali metal tert.-butoxide or other alkali metal, t.-alkanolate in DMSO, DMF, benzene, toluene, xylene, sulfolane or a t.-alkanol corresponding to the alkanolate employed, or by treatment with sodium or potassium lower alkanolate, sodium hydride, potassium-sodium amalgam (1:1) lithio or sodio-N-methylaniline, to form the 3-amino-4-cyano-2H-1,5 benzodioxepin G. Best results are obtained when this step is carried out in an inert atmosphere such as under nitrogen or other inert gas such as argon or other usual inert gas. Intermediate $G^1$ is hydrolyzed and decarboxylated to the ketone A either by first refluxing in aqueous acetic acid followed by refluxing with phosphoric acid, or by acid alcoholysis followed by heating in aqueous alkanol to effect hydrolysis and decarboxylation. While intermediate $G^1$ is illustrated as having the structure 3-amino-4-cyano, its tautomer, 3-imino-4-cyano-3,4-dihydro-2H-1,5-benzodioxepin may also be present. It is understood that when $X, X^1$, R and/or $R^1$ is/are other than hydrogen, additional isomers are possible. However, upon hydrolysis with concomitant decarboxylation by either of the above procedures all tautomers or isomers are converted to the 3-keto compound A.

When $X, X^1$, and all R's in compound A are hydrogen, this product, if desired, can be reacted with an azacycle such as morpholine, piperidine, pyrrolidine, and the like to give the 3-azacyclic substituted compound H which when treated with an alkylating agent as a lower alkyl iodide or bromide, dialkylsulfate or trialkyloxoniumtetrafluoroborate, provides the desired 2-mono-substituted-3-keto compound A.

The second of the principal methods for making compound A from the catechol E involves initial reaction of E with a halo-alkanoic acid ester, halo-$CR^2R^3$-$CO_2$alkyl, to give the 1,2-bis-alkoxycarbonylalkoxybenzene, $F^2$. When $R^2$ and $R^3$ in compound $F^2$ are each hydrogen, compound $F^2$ is produced in one step. When $R^2$ and/or $R^3$ are other than hydrogen, then the catechol ($X-X^1-R-R^1-H$) initially is treated with haloacetic acid ester, the ortho-alkoxycarbonylmethoxyphenol isolated and then reacted with a haloalkanoic acid ester to give $F^2$ wherein $R^2$ and/or $R^3$ are other than hydrogen. When $X, X^1$, R and/or $R^1$ is/are other than hydrogen, preferably the appropriate salicylaldehyde is reacted with Z—$CR^2R^3CO_2$alkyl wherein $R^2$ and/or $R^3$ is other than hydrogen and the resulting compound oxidized by peracetic acid followed by mild hydrolysis to give the ortho-alkoxycarbonylalkoxyphenol or the corresponding acid which can be reesterified. The ester then is treated with an alkyl haloacetate to provide intermediate $F^2$. Cyclization of compound "$F^2$" to form $G^2$ is effected by substantially the same method described above for the cyclization of $F^1$ to provide G1. Hydrolysis and decarboxylation of $G^2$ by acid hydrolysis in a lower alkanol advantageously by employing aqueous hydrochloric acid in mathanol or ethanol followed by heating gives the desired 3-keto compound A.

The pharmacologically acceptable salts of the benzodioxepins of this invention are prepared by the reaction of product I with an inorganic or organic acid such as hydrochloric, hydrobromic, sulfuric, phosphoric, formic, acetic, succinic, lactic, malic, tartaric, citric, maleic, phenylacetic, benzoic, salicyclic, or p-toluenesulfonic acid or similar acids that are known to provide pharmacologically acceptable salts.

The benzodioxepins however can be employed in pharmaceutical formulations either in the form of free bases or in the form of their acid addition salts in conjunction or admixture with organic or inorganic solid or liquid pharmaceutical excipients. These pharmaceutical formulations can be in the form of tablets, solutions, suspensions, emulsions, or aerosols suitable for oral or topical administration.

Unlike hitherto known bronchodilators which generally are short acting, the benzodioxepin products of this invention exhibit a long duration of activity. The compounds were found when tested according to accepted and standard laboratory procedures in guinea pigs to be orally effective within a dosage range of from about 1 mg. to about 20 mg./kg. and when administered intravenously the effective dosage range was between 10 microg./kg. to 2 mg./kg. At these dosages the products were acceptably tolerated by the animals.

The 3'-$R^6$-6-R-7-$R^1$-3,4-dihydro-2H-1,5-benzodioxepin-3-spiro-5'-oxazolidin-2'-one compounds prepared in the synthesis of the principal products of this invention, are also novel and form another feature of this invention. In addition to exhibiting bronchodilating properties, these compounds also exhibit muscle relaxing properties and are therefore useful in the relief of spastic states.

The following examples will illustrate the preparation of representative products of this invention prepared by the above-described procedures. It will be understood that while all of the compounds can be prepared by the procedure described in the following examples, modifications of the procedural steps which would be obvious to the skilled chemist can be employed. The following examples therefore are not to be considered as limiting the preparation of any particular compound to the precise procedural steps described in the examples which are provided solely to illustrate the best mode currently known to applicant.

Where the term benzodioxepin is employed in the disclosure and claims it is to be understood to mean 3,4-dihydro-2H-1,5-benzodioxepin.

The following examples describe the preparation of the novel products of this invention by the route A → C → D → I illustrated in Flow Diagram I.

EXAMPLE 1

3-hydroxy-3-isopropylaminomethyl-3,4-dihydro2H-1,5 benzodioxepin Hydrochloride

Step A.—Preparation of 1,2-di-(cyanomethoxy)benzene:

A mixture of 99 g. (0.9 moles) of catechol, 90.6 g. (1.2 moles) of chloroacetonitrile, 168 g. (1.22 moles) of finely powdered potassium carbonate, and 600 ml. of acetone is refluxed with stirring for 1½ hours. The mixture is treated with 45.3 g. (0.6 mole) of chloroacetonitrile and 84 g. (0.608 mole) of potassium carbonate, and refluxed for a further 3.5 hours. The mixture is filtered, the solids washed with 150 ml. of acetone and the combined filtrate evaporated in vacuo to give an oil. The oil which crystallizes is recrystallized from ethanol-water (8:1) to give 138 g. (81.5%) of 1,2-di-(cyanomethoxy)benzene, M.P. 85.0°–86.5° C. Further recrystallization from the same solvent system affords the product melting at 85.0°–85.5° C.

Analysis calculated for $C_{10}H_6N_2O_2$: C, 63.82; H, 4.29; N, 14.89; Found: C, 64,17; H, 4.48; N, 14.94.

Step B: Preparation of 3-amino-4-cyano-2H-1,5-benzodioxepin

Sodamide (49.2 g., 1.26 mole) is added with stirring under nitrogen to 370 ml. of dry dimethyl sulfoxide. After the initial vigorous evolution of ammonia has subsided the solution is heated one-half hour at 60° C. A solution of 115.8 g. (0.616 mol) of 1,2-di-(cyancmethoxy)benzene in 246 ml. of dimethyl sulfoxide is added with stirring and cooling (water bath at ambient temperature) during 1 hour and the reaction mixture stirred for a further two hours at ambient temperature. A mixture of 81.5 ml. of acetic acid and 246 ml. of water is added slowly accompanied by stirring and cooling. The mixture is poured into 1.2 liters of water and the tan-colored solids collected. The solids are recrystallized from chloroform to give 75.5 g. (65%) of 3-amino-4-cyano-2H-1,5-benzodioxepin, M.P. 167°–169° C. Further recrystallization from chloroform affords the product melting at 168°–169° C.

Analysis calculated for $C_{10}H_8N_2O_2$: C, 63.82; H, 4.29; N, 14.890 Found: C, 63.80; H, 43.5; N, 14.70.

Alternatively the above 3-amino-4-cyano-2H-1,5-benzodioxepin can be prepared as follows.

A solution of 9.4 g. (50 millimoles) of 1,2-di(-cyanomethoxy)benzene in 20 ml. of dimethyl sulfoxide is added under nitrogen to a stirred mixture of 12.3 g. (110 millimoles) of potassium tert.-butoxide in 30 ml. of dimethyl sulfoxide cooled in a water bath at ambient temperature. The mildly exothermic reaction raises the internal temperature of the mixture to 42° C. The mixture is stirred a further 2 hours and a solution of 6.6 ml. of acetic acid in 20 ml. of water added slowly with cooling. [Alternatively, the reaction mixture can be poured into the aqueous acetic acid solution.] The product is precipitated by pouring the mixture into 100 ml. of water. The beige-colored solid is collected, washed with water, and air dried to give 9.5 g. of crude product, m.p. 148°–154° C. Thr crude product is recrystallized from 200 ml. of chloroform to afford 5.8 g. (61.7%) of 3-amino-4-cyano-2H-1,5-benzodioxepin. A mixed melting point with the product obtained above gave no depression.

Step C: Preparation of 3-oxo-3,4-dihydro-2H-1,5-benzodioxepin

A mixture of 16.0 g. (85.1 millimoles) of 3-amino-4-cyano-2H-1,5-benzodioxepin, 18 ml. of water, and 300 ml. of acetic acid is refluxed ½ hour. The mixture is treated dropwise with 120 ml. 85% phosphoric acid and then refluxed overnight. The solution is cooled to ambient temperature, and poured onto 500 g. of crushed ice. Ammonium sulfate (180 g.) is added and the solution continuously extracted with ether for several hours. The ethereal solution is evaporated to dryness to remove ether and acetic acid, and the residual oil dissolved in diethyl ether, washed with 10% sodium carbonate solution, dried, and evaporated. The resulting oil is fractionated to give 8.96 g. (64%) of 3-oxo-3,4-dihydro-2H-1,5-benzodioxepin, b.p. 52°–61° C, at 0.07 mm pressure, which at first is a colorless oil which solidifies. The product is used directly in the next step.

STEP D:

Preparation of 3-hydroxy-3-cyano-3,4-dihydro-2H-1,5-benzodioxepin

A solution of 13.5 g. (208 millimoles) of potassium cyanide in 27 ml. of water is added dropwise to a mixture of 18.7 g. (114 millimoles) of 3-oxo-3,4-dihydro-2H-1,5-benzodioxepin and 21.2 g. (208 millimoles) of acetic anhydride with stirring and cooling. The mixture is stirred at ambient temperature overnight and then is made alkaline with 10% sodium carbonate solution. The product in the form of an oil is extracted with diethyl ether, treated with charcoal and dried over calcium sulfate. Evaporation of the solvent gives a solid that is recrystallized from carbon tetrachloride to give 3-hydroxy-3-cyano-3,4-dihydro-2H-1,5-benzodioxepin as plates, m.p. 108.5°–110° C.

Analysis calculated for $C_{10}H_9NO_3$: C, 62.82; H, 4.74; N, 7.33; Found: C, 62.70; H, 4.52; N, 7.09.

An alternative method for preparing 3-hydroxy-3-cyano-3,4-dihydro-2H-1,5-benzodioxepin can be carried out in the following manner.

To a stirred solution of 4.92 g. (30 millimoles) of 3-oxo-3,4-dihydro-2H-1,5-benzodioxepin in 100 mls. of benzene is added dropwise a solution of 30 millimoles of anhydrous hydrogen cyanide in 50 ml. of benzene. The reaction mixture is stirred overnight at ambient temperature, basified with 10% sodium carbonate solution and the organic layer separated. The benzene solution is washed once with water and dried successively over anhydrous magnesium sulfate and calcium sulfate. Evaporation of the solvent under reduced pressure at 40° C. yields the crude cyanohydrin which upon purification and mixed melting point determination gives no depression with an authentic sample of 3-hydroxy-3-cyano-3,4-dihydro-2H-1,5-benzodioxepin.

STEP E:

Preparation of 3-hydroxy-3-minomethyl-3,4-dihydro-2H-1,5-benzodioxepin hydrochloride A mixture of 9.5 g. (49.7 millimoles) of 3-hydroxy-3-cyano-3,4-dihydro-2H-1,5-benzodioxepin, 75 ml. of anhydrous ethanol, and 3 ml. of acetic acid is shaken under hydrogen at ambient temperature and pressure in the presence of 100 mg. of platinum oxide and a little ethanolic-hydrogen chloride. The catalyst is removed and the filtrate evaporated to dryness to give 5.2 g. of crude product, m.p. 207°–214° C. Recrystallization of this crude product from isopropanol afford 3-hydroxy-3-aminomethyl-3,4-dihydro-2H-1,5-benzodioxepin hydrochloride, m.p. 228°–230° C. (clearing at 238° C.)

Analysis calculated for $C_{10}H_{13}NO_3 \cdot HCl$: C, 51,84: H, 6.09; N, 6.06; Found: C, 52.11; H, 6.13; N, 5.86.

An alternative method for preparing 3-hydroxy-3-aminomethyl-3,4-dihydro-2H-1,5-benzodioxepin can be carried out in the following manner.

3-Hydroxy-3-cyano-3,4-dihydro-2H-1,5-benzodioxepin (30 millimoles) is dissolved in 100 ml. of dry diethyl ether and the solution added dropwise during a period of 0.75 hours under dry nitrogen to a stirred slurry of 3.8 g. (100 millimoles) of lithium aluminum hydride in 100 ml. of dry ether. The mixture is stirred under reflux for 2.25 hours and treated carefully with 3.8 ml. of water. An easily-filterable precipitate of metallic compounds is obtained by the dropwise addition of 5.7 ml. of 10% sodium hydroxide solution followed by 11.4 ml. of water. The ethereal solution is filtered and the filter-cake then is washed with 50 ml. of diethyl ether. The combined filtrate is dried over anhydrous magnesium sulfate and again over calcium sulfate before evaporation in a rotary film-evaporator to yield 5.13 g. (87%) of the free base as a colorless solid m.p. 60°–63° C. (to a turbid melt). This product, upon recrystallization from benzene from which it separates as colorless plates melts at 66°–68° C. A solution of 3.0 g. of the base dissolved in dry diethyl ether is treated with a slight excess of approximately 5N ethanolic-hydrogen chloride solution affording 2.82 g. of 3-hydroxy-3-aminomethyl-3,4-dihydro-2H-1,5-benzodioxepin hydrochloride. This product gives no depression in melting point when admixed with authentic material prepared by the catalytic reduction of the cyanohydrin, as described above.

STEP F:

Preparation of
3-hydroxy-3-isopropylaminomethyl-3,4-dihydro-2H-1,5-benzodioxepin hydrochloride A mixture of 3.92 g. (16.95 millimoles) of 3-hydroxy-3-aminomethyl-3,4-dihydro-2H-1,5-benzodioxepin hydrochloride, 1.39 g. (16.95 millimoles) of anhydrous sodium acetate, and 80 ml. of anhydrous ethanol is stirred under nitrogen for 20 minutes. Acetone (1.08 g., 18.6 millimoles) is added and the mixture stirred for 30 minutes. The mixture is hydrogmated at ambient temperature and pressure for 1½ hours over 100 mg. of platinum oxide. The catalyst is removed, the solution evaporated to a syrup, 60 ml. of dry diethyl ether added, and a slight excess of 9.7N ethanolic-hydrogen chloride solution added. The solids are collected to give 4.65 g. of crude product, m.p. 172°–175°C. The product is recrystallized from isopropanol to give 3.05 g. (65%) of 3-hydroxy-3-isopropylaminomethyl-3,4-dihydro-2H-1,5-benzodioxepin hydrochloride, m.p. 178.5°–180.0° C.

Analysis calculated for $C_{13}H_{19}NO_3$·HCl: C, 57.04; H, 7.36; N, 5.11; Found: C, 56.95; H, 7.29; N, 4.89.

An alternative method for preparing the benzodioxepin of step F can be carried out in the following manner.

3-Hydroxy-3-aminomethyl-3,4-dihydro-2H-1,5-benzodioxepin (195 mg., 1 millimole) is dissolved in isopropanol (3 ml.) and treated with acetone (64 mg., 1.1 millimoles). On standing overnight, the solution deposits a crystalline solid (glistening plates), and this is reduced in situ by the addition of sodium borohydride (75.6 mg., 2 millimoles). After stirring the mixture at ambient temperature for 3 hours water (20 ml.) is added and then 2.75N hydrochloric acid (1.5 ml.). The solution is extracted with ether (10 ml.) and the extract rejected. Glycerol (1 ml.) is added and the solution then is basified with 2N sodium hydroxide (5 ml.) to liberate the free base. The latter is extracted with ether (25 ml.), the ethereal solution washed with water (2 × 10 ml.) and then dried thoroughly over magnesium sulphate followed by calcium sulphate. Addition of 5N ethanolic hydrogen chloride solution to the solution of base precipitated the 3-hydroxy-3-isopropylaminomethyl-3,4-dihydro-2H-1,5-benzodioxepin hydrochloride (136 mg., 49.6%). No depression of melting point is observed when the product is admixed with an authentic specimen of the compound.

EXAMPLE 2

3-hydroxy-3-quanidinomethyl-3,4-dihydro-2H-1,5-benzodioxepin sulfate 3-hydroxy-3-aminomethyl-3,4-dihydro-2H-1,5-benzodioxepin from Example 1, Step E, (1.95 g., 10 millimoles) and 2.78 g. (10 millimoles) of S-methylisothiourea sulfate in 15 mls. of dimethylformamide and 2 mls. of water is heated at 90°–100° C. for 5 hours. The solvent is evaporated in vacuo and the residue recrystallized from ethanol to give 3-hydroxy-3-guanidinomethyl-3,4-dihydro-2H-1,5-benzodioxepin sulfate.

EXAMPLE 3

3-Hydroxy-3-(3-phenylguanidinomethyl)-3,4-dihydro-2H-1,5-benzodioxepin hydriodide A mixture of S-methyl-N-phenylisothiourea hydriodide (2.94 g., 10 millimoles), 3-hydroxy-3-aminomethyl-3,4-dihydro-2H-1,5-benzodioxepin 1.95 g. (10 millimoles) from Example 1, Step E, and 20 mls. of ethanol is warmed until evolution of methyl mercaptan ceases and then is refluxed for two hours. The solution then is evaporated to a small volume and diluted with ether to give 3-hydroxy-3-(3-phenylguanidinyl)-methyl-3,4-dihydro-2H-1,5-benzodioxepin hydriodide.

EXAMPLE 4

3-hydroxy-3-(3-ethylguanidinyl)methyl-3,4-dihydro 2H-1,5-benzodioxepin hydiodide A mixture of S-methyl-N-ethylisothiourea hydriodide (2.46 g., 10 millimoles), 3-hydroxy-3-aminomethyl-3,4-dihydro-2H-1,5-benzodioxepin 1.95 g. (10 millimoles) from Example 1, Step E, and 20 ml. of ethanol is refluxed for four hours. The solution then is evaporated to a small volume and diluted with ether to afford 3-hydroxy-3-(3-ethylguanidinyl)methyl-3,4-dihydro-2H-1,5-benzodioxepin hydriodide.

EXAMPLE 5

3-hydroxy-3-[(2-phenylcyclohexyl)aminomethyl]-3,4-dihydro-2H-1,5-benzodioxepin hydrochloride By replacing the acetone employed in Example 1, Step F (or alternate Step F) by an equivalent quantity of 2-phenylcyclohexanone and then following essentially the same procedures described therein, there is obtained 3-hydroxy-3-[(2-phenylcyclohexyl)aminomethyl]-3,4-dihydro-2H-1,5-benzodioxepin hydrochloride, m.p. 213.5–215° C.

EXAMPLE 6

3-Hydroxy-3-([2-(3-cyclohexyl)propyl]aminomethyl)-3,4-dihydro-2H-1,5-benzodioxepin hydrochloride By replacing the acetone employed in Example 1, Step F (or alternate Step F) by an equivalent quantity of cyclohexylacetone and then following essentially the same procedure described therein, there is obtained 3-hydroxy-3-([2-(3-cyclohexyl)propyl]aminomethyl-3,4-dihydro-2H-1,5-benzodioxepin hydrochloride.

EXAMPLE 7

3-hydroxy-3-dimethylaminomethyl-3,4-dihydro-2H-1,5-benzodioxepin hydrochloride

3-Hydroxy-3-aminomethyl-3,4-dihydro-2H-1,5-benzodioxepin (3.2 g., 0.0164 mole) from Example 1, Step E, is added to formic acid (4.3 g., 0.082 mole). Formalin (3 ml.), is added and the solution then heated on a steam bath for 17 hours. The yellow liquid is stripped, basified with 20% sodium hydroxide (10 ml.) and twice extracted with ether (50 ml.). The ether extracts are combined and washed with water, then dried over magnesium sulfate and calcium sulfate then evaporated yielding 3.4 g. of an oil which upon acidification with ethanolic-hydrogen chloride crystallizes as the hydrochloride melting at 118°–120° C.

EXAMPLE 8

3-Hydroxy-3-methylaminomethyl-3,4-dihydro-2H-1,5-benzodioxepin hydrochloride

Step A: preparation of 3-hydroxy-3-formamidomethyl-3,4-dihydro-2H-1,5-benzodioxepin A mixture of 1.49 g. of 97% formic acid and 3.21 g. of acetic anhydride is heated in a water bath for 2 hours (internal temperature did not exceed 55° C.) then cooled and added dropwise to a slurry of 5.86 g. of 3-hydroxy-3-aminomethyl-3,4-dihydro-2H-1,5-benzodioxepin from Example 1, Step E, in 60 ml. anhydrous ether. A gummy white solid forms which slowly dissolves with stirring at ambient temperature overnight. The clear liquid obtained is washed twice with water, twice with 10% sodium carbonate and twice with water. The ether then is evaporated affording 2.5 g. of semi-solid material.

An oil, insoluble in either water or ether, is collected with the water and then removed by shaking the mixture with chloroform. Upon stripping the chloroform layer there is obtained 3.6 g. of 3-hydroxy-3-formamidomethyl-3,4-dihydro-2H-1,5-benzodioxepin in the form of a semi-solid.

Step B: Preparation of 3-methylaminomethyl-3,4-dihydro-2H-1,5-benzodioxepin hydrochloride 3-hydroxy-3-formamidomethyl-3,4-dihydro-2H-1,5-benzodioxepin (5.8 g.) in 200 ml. anhydrous ether is added to lithium aluminum hydride (2.0 g.) in 40 ml. of anhydrous ether dropwise in one hour. The mixture then is refluxed for 2 hours and the excess lithium aluminum hydride then decomposed with water (5.0 ml.) followed by 10% sodium hydroxide (3.6 ml.) followed by 6.0 ml. of water. The white solid formed is filtered and the filtrate dried over magnesium sulfate then over calcium sulfate. It is stripped affording 3.8 g. of oil. The oil is acidified with 11N hydrochloric acid in ethanol to give 3.7 g. of 3-hydroxy-3-methylaminomethyl-3,4-dihydro-2H-1,5-benzodioxepin hydrochloride, m.p. 189°–205°C. Following several recrystallizations from ethanol, the product melts at 217–219°C.

Other benzodioxepins prepared by the methods described in Example 1 are identified in Table I. In particular the ketone, acetone, employed in Step F of Example 1 is replaced by the carbonyl compound identified in the following table, which, following substantially the same procedure there described, gives the benzodioxepins I having the $R^6$ substituent specified in Table I.

TABLE I

"D" + Carbonyl Reactant → Example 1, Step F Method → "I"

| Ex. No. | Carbonyl Reactant | $R^6$ | Empirical Formula | m.p. °C. | | C | H | Analysis Cl | N | P |
|---|---|---|---|---|---|---|---|---|---|---|
| 9 | $C_2H_5-\underset{CH_3}{\overset{}{C}}=O$ | $-CH(CH_3)(C_2H_5)$ | $C_{14}H_{21}NO_3 \cdot HCl$ | 183–184 | Calc. Found | 58.43 58.66 | 7.71 7.66 | 12.32 12.55 | 4.87 4.83 | |
| 10 | $HO-\bigcirc-CH_2\underset{CH_3}{\overset{}{C}}=O$ | $-CH(CH_3)-CH_2-\bigcirc-OH$ | $C_{19}H_{23}NO_4 \cdot H_3PO_4$ | 127–129 | Calc. Found | | | | 3.28 3.28 | 7.25 7.38 |
| 11 | $\bigcirc_N-CH_2\underset{CH_3}{\overset{}{C}}=O$ | $-CH(CH_3)-CH_2-\bigcirc_N$ | $C_{21}H_{24}N_2O_3 \cdot HCl$ | 190–191 (dec.) | Calc. Found | 64.86 64.65 | 6.48 6.46 | 9.12 9.25 | 7.20 7.13 | |
| 12 | $Cl-\bigcirc-CH_2-\underset{CH_3}{\overset{}{C}}=O$ | $-CH(CH_3)-CH_2-\bigcirc-Cl$ | $C_{19}H_{22}ClNO_3 \cdot HCl$ | 163–165 | Calc. Found | 59.38 59.56 | 6.03 6.15 | 18.45 18.30 | 3.64 3.83 | |
| 13 | $\bigcirc-(CH_2)-\underset{CH_3}{\overset{}{C}}=O$ | $-CH(CH_3)-(CH_2)_2-\bigcirc$ | $C_{20}H_{25}NO_3 \cdot HCl$ | 180–183 | Calc. Found | 66.02 66.12 | 7.20 7.12 | 9.74 9.65 | 3.85 3.91 | |
| 14 | $CH_3-CHO$ | $-C_2H_5$ | $C_{12}H_{17}NO_3 \cdot HCl$ | 181.5–183 | Calc. Found | 55.49 55.72 | 6.99 6.73 | 13.65 13.49 | 5.39 5.49 | |
| 15 | $\bigcirc-CHO$ | $-CH_2-\bigcirc$ | $C_{17}H_{19}NO_3 \cdot HCl$ | 214–216 | Calc. Found | 63.45 63.62 | 6.26 6.39 | 11.02 10.89 | 4.35 4.37 | |
| 16 | $\bigcirc-CH_2-CHO$ | $-(CH_2)_2-\bigcirc$ | $C_{18}H_{21}NO_3 \cdot HCl$ | 229–231 | Calc. Found | 64.38 64.39 | 6.60 6.27 | 10.56 10.74 | 4.17 4.23 | |
| 17 | $\bigcirc-CH_2-\underset{CH_3}{\overset{}{C}}=O$ | $-CH(CH_3)CH_2-\bigcirc$ | $C_{19}H_{23}NO_3 \cdot HCl$ | 170–174 | Calc. Found | 65.23 65.59 | 6.91 6.89 | 10.13 10.20 | 4.00 4.14 | |
| | | | $C_{20}H_{23}NO_5 \cdot HCl$ | 188–189 | Calc. | 60.00 | 6.14 | 9.00 | 3.56 | |

TABLE I-continued

"D" + Carbonyl Reactant →(Example 1, Step F Method)→ "I"

| Ex. No. | Carbonyl Reactant | R[6] | Empirical Formula | m.p. °C. | | Analysis | | | | |
|---|---|---|---|---|---|---|---|---|---|---|
| | | | | | | C | H | Cl | N | P |
| 18 | (structure with CH₃) | -CH(CH₃)-CH₂-(aryl) | | .5 | Found | 61.02 | 6.14 | 8.91 | 3.38 | |
| 19 | (trimethoxy structure) | -CH(CH₃)-CH₂-(trimethoxyaryl) | $C_{22}H_{29}NO_6 \cdot HCl$ | 220–221–.5 | Calc. | 60.06 | 6.87 | 8.06 | 3.18 | |
| | | | | | Found | 60.24 | 6.91 | 7.96 | 3.09 | |
| 19-a | (benzodioxepin ketone) | (benzodioxepin) | $C_{19}H_{21}NO_5$ | 112–114 | Calc. | 66.46 | 6.16 | | 4.08 | |
| | | | | | Found | 66.56 | 6.14 | | 3.65 | |

Table II also describes additional products made by the procedure of Example 1. The products identified here are prepared by replacing the catechol employed in Step A of Example 1 by an equimolecular quantity of the catechol "E" having the R and R[1] substituents given in the table which is carried through the procedures described in Steps A - E of Example 1 to provide the 3-hydroxy-3-aminomethyl compound D. Compound D thus obtained upon reaction with acetone according to the procedure described in Step F of Example 1 provides the 3,3-disubstituted I having the substituents R and R[1] given in Table II.

EXAMPLE 23

3-hydroxy-3-(1-isopropylaminoethyl)-3,4-dihydro-2H-1,5-benzodioxepin hydrochloride Step A.—Preparation of 3-hydroxy-3-(1-nitroethyl)-3,4-dihydro-2H-1,5-benzodioxepin:

To a solution of 3-oxo-3,4-dihydro-2H-1,5-benzodioxepin (9.84 g., 60 millimoles) prepared as described in Example 1, Steps A–C in anhydrous ethanol (30 ml.)

TABLE II

"E" →(Example 1, Steps A-E Methods)→ "D" →(Example 1, Step F Method)→ "I"

| Example No. | R | R[1] | Empirical Formula | m.p. °C. | | Analysis | | | |
|---|---|---|---|---|---|---|---|---|---|
| | | | | | | C | H | Cl | N |
| 20 | H | CH₃ | $C_{14}H_{21}NO_3 \cdot HCl$ | 175–177 | Calc. | 58.42 | 7.71 | 12.32 | 4.87 |
| | | | | | Found | 58.66 | 7.70 | 12.53 | 5.00 |
| 21 | H | Cl | $C_{13}H_{18}ClNO_3 \cdot HCl$ | 171–172.5 | Calc. | 50.66 | 6.21 | 23.01 | 4.54 |
| | | | | | Found | 50.49 | 6.17 | 23.15 | 4.69 |
| 22 | —OCH₃ | H | $C_{14}H_{21}NO_4 \cdot C_4H_4O_4$ | 155–157 | Calc. | 56.39 | 6.57 | | 3.65 |
| | | | | | Found | 56.38 | 6.51 | | 3.97 |

The preparation of the benzodioxepin bearing an R[4] substituent by the reaction of the 3-keto intermediate "A" with a nitro-alkane, thus following the route A → B → D → I is illustrated by the examples below. It will be understood that other nitro-alkanes and other 3-oxo-benzodioxepins can be employed as starting materials as well as other aldehydes or ketones of the type described as suitable above. It also is possible to employ the nitro-alkane in the route A → B → D → E → I shown in Flow Diagram I.

is added nitro-ethane (10 ml.) and the mixture cooled to 0°–5° C. A solution of sodium (1.5 g., 65 millimoles) in anhydrous ethanol (30 ml.) then is added dropwise with stirring at about 5° C. Stirring is continued at this temperature for 1 hour and for another hour at ambient temperature. Dry ether (60 ml.) is added and the mixture then stirred overnight. More dry ether (60 ml.) is added and the solid is collected after stirring the mixture for 2 hours to give 5.73 g. of product after drying in a desiccator.

Evaporation of the mother liquors to a syrup and dilution with dry ether (ca. 50 ml.) yielded a further 5.32 g. of product.

Treatment of a suspension of the combined yield of product in dry ether with a slight excess of acetic acid liberated 3-hydroxy-3-(1-nitroethyl)-3,4-dihydro-2H-1,5-benzodioxepin which is isolated from the ethereal solution after washing the latter with water and then drying it thoroughly first over magnesium sulfate and then over calcium sulfate.

Step B.—Preparation of 3-(1-aminoethyl)-3-hydroxy-3,4-dihydro-2H-1,5-benzodioxepin hydrochloride:

The crude nitro compound (5.34 g., 22.3 millimoles) dissolved in a mixture of ethanol (30 ml.) and acetic acid (2 ml.) is hydrogenated at 45° C. and atmospheric pressure in the presence of Raney nickel (ca. 2.5 g.). On working up the product as its hydrogen chloride salts as described in Step E of Example 1, there is obtained 3-(1-amiinoethyl)-3-hydroxy-3,4-dihydro-2H-1,5-benzodioxepin hydrochloride, m.p. 178°–183° C. after crystallization from a mixture of isopropanol and ether.

Analysis calculated for $C_{11}H_{15}NO_3 \cdot HCl$: C, 53.77; H, 6.56; CL, 14.43; N, 5.70. Found: C, 54.00; H, 6.58; Cl, 14.68; N, 5.79.

Step C.—Preparation of 3-hydroxy-3-(1-isopropylaminoethyl)-3,4-dihydro-2H-1,5-benzodioxepin hydrochloride:

By replacing the 3-hydroxy-3-aminomethyl-3,4-dihydro-2H-1,5-benzodioxepin hydrochloride employed in Step F of Example 1 by an equivalent quantity of 3-hydroxy-3-(1-aminoethyl)-3,4-dihydro-2H-1,5-benzodioxepin hydrochloride and employing the same reaction conditions called for in Example 1, Step F, there is obtained 3-hydroxy-3-(1-isopropylaminoethyl)-3,4-dihydro-2H-1,5-benzodioxepin hydrochloride, M.P. 206°–211° C. It was purified by recrystallization from ethanol giving a product of M.P. 215°–7°.

$C_{14}H_{21}NO_3$, HCl requires: C, 58.43; H, 7.71; Cl, 12.32; N, 4.87. Found: C 58.43; H, 7.55; Cl, 12.59; 5.04.

EXAMPLE 24

3-Hydroxy-3-[1-(isopropylamino)propyl]-3,4-dihydro-2H-1,5-benzodioxepin Hydrochloride

Step A: Preparation of 3-hydroxy-3-(1-aminopropyl)-3,4-dihydro-2H-1,5-benzodioxepin hydrochloride By following the procedures described in Steps A and B of Example 23, but replacing the nitro-ethane by an equivalent quantity of 1-nitropropane, there is obtained 3-hydroxy-3-(1-aminopropyl)-3,4-dihydro-2H-1,5-benzodioxepin hydrochloride, m.p. 197°–198° C. after crystallization from isopropanol.

Analysis calculated for $C_{12}H_{17}NO_3 \cdot HCl$: C. 55.49; H, 6.99; Cl, 13.65; N, 5.39: Found: C, 55.28; H, 7.04; Cl, 13.99; N, 5.57.

Step B: Preparation of 3-hydroxy-3-[1-(isopropylamino)propyl]-3,4-dihydro-2H-1,5-benzodioxepin hydrochloride This product is prepared by the procedure described in Example 1, Step F, except the 3-hydroxy-3-aminomethyl-3,4-dihydro-2H-1,5-benzodioxepin employed therein is replaced by an equivalent quantity of 3-hydroxy-3-(1-aminopropyl)-3,4-dihydro-2H-1,5-benzodioxepin.

By following the procedure called for in Example 23, Step C, but employing the carbonyl reactant identified in Table III, there are obtained additional products I having an $R^4$ substituent. Illustrative examples are provided in the following Table.

TABLE III

"D" + Carbonyl Reactant $\xrightarrow{\text{Example 1, Step F Method}}$ "I"

| Example No. | "D" Intermediate from Example | $R^4$ | Carbonyl Reactant | $R^5$ |
|---|---|---|---|---|
| 25 | 23 | —CH₃ | $C_2H_5-\underset{CH_3}{\overset{|}{C}}=O$ | —CH(CH₃)(C₂H₅) |
| 26 | 23 | —CH₃ | indolyl-CH₂-C(CH₃)=O | -CH(CH₃)-CH₂-indolyl |
| 27 | 24 | —CH₂CH₃ | indolyl-CH₂-C(CH₃)=O | -CH(CH₃)-CH₂-indolyl |
| 28 | 23 | —CH₃ | HO-C₆H₄-CH₂-C(CH₃)=O | -CH(CH₃)-CH₂-C₆H₄-OH |
| 29 | 24 | —CH₂CH₃ | HO-C₆H₄-CH₂-C(CH₃)=O | -CH(CH₃)-CH₂-C₆H₄-OH |

TABLE III-continued

"D" + Carbonyl Reactant → (Example 1, Step F Method) → "I"

| Example No. | "D" Intermediate from Example | R⁴ | Carbonyl Reactant | R⁵ |
|---|---|---|---|---|
| 30 | 23 | —CH₃ | (C₆H₅)-CH₂-C(CH₃)=O | -CH(CH₃)CH₂-(C₆H₅) |
| 31 | 23 | —CH₃ | Cl-(C₆H₄)-CH₂-C(CH₃)=O | -CH(CH₃)-CH₂-(C₆H₄)-Cl |
| 32 | 24 | —CH₂CH₃ | (C₆H₅)-CH₂-C(CH₃)=O | -CH(CH₃)CH₂-(C₆H₅) |
| 33 | 23 | —CH₃ | (C₆H₅)-CH₂-CHO | -(CH₂)₂-(C₆H₅) |
| 34 | 23 | —CH₃ | CH₃—CHO | —C₂H₅ |
| 35 | 23 | —CH₃ | (C₆H₅)-CHO | -CH₂-(C₆H₅) |
| 36 | 24 | —CH₂CH₃ | methylenedioxyphenyl-CH₂-C(CH₃)=O | -CH(CH₃)-CH₂-(methylenedioxyphenyl) |
| 37 | 23 | —CH₃ | 3,4,5-trimethoxyphenyl-CH₂-C(CH₃)=O | -CH(CH₃)-CH₂-(3,4,5-trimethoxyphenyl) |
| 38 | 24 | —CH₂CH₃ | (C₆H₅)-(CH₂)₂-C(CH₃)=O | -CH(CH₃)-(CH₂)₂-(C₆H₅) |
| 39 | 24 | —CH₂CH₃ | CH₃—CHO | —C₂H₅ |
| 40 | 23 | —CH₃ | (C₆H₅)-(CH₂)₂-C(CH₃)=O | -CH(CH₃)-(CH₂)₂-(C₆H₅) |
| 41 | 23 | —CH₃ | methylenedioxyphenyl-CH₂-C(CH₃)=O | -CH(CH₃)-CH₂-(methylenedioxyphenyl) |

Additional illustrative examples of products made by Example 23 procedure are provided in Table IV.

TABLE IV

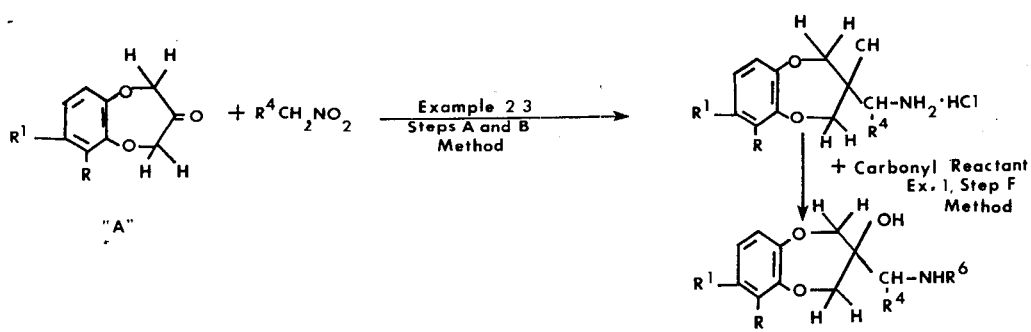

| Ex. No. | "A" Intermediate from Example | R | $R^1$ | $R^4$ | Carbonyl Reactant | $R^5$ |
|---|---|---|---|---|---|---|
| 42 | 20 | H | —$CH_3$ | —$CH_3$ | $(CH_3)_2C=O$ | —$CH(CH_3)_2$ |
| 43 | 20 | H | —$CH_3$ | —$CH_3$ | $C_2H_5$–$\underset{CH_3}{C}$=O | —$CH(CH_3)(C_2H_5)$ |
| 44 | 22 | —$OCH_3$ | H | —$CH_3$ | HO–⟨⟩–$CH_2$–$\underset{CH_3}{C}$=O | –$CH(CH_3)$–$CH_2$–⟨⟩–OH |
| 45 | 21 | H | Cl | —$CH_3$ | HO–⟨⟩–$CH_2$–$\underset{CH_3}{C}$=O | –$CH(CH_3)$–$CH_2$–⟨⟩–OH |
| 46 | 21 | H | Cl | —$CH_2CH_3$ | (indolyl)-$CH_2$-$\underset{CH_3}{C}$=O | –$CH(CH_3)$–$CH_2$–(indolyl) |
| 47 | 20 | H | —$CH_3$ | —$CH_3$ | methylenedioxyphenyl-$CH_2$-$\underset{CH_3}{C}$=O | –$CH(CH_3)$–$CH_2$–(methylenedioxyphenyl) |
| 48 | 22 | —$OCH_3$ | H | —$CH_2CH_3$ | (indolyl)-$CH_2$-$\underset{CH_3}{C}$=O | –$CH(CH_3)$–$CH_2$–(indolyl) |
| 49 | 22 | —$OCH_3$ | H | —$CH_2CH_3$ | ⟨⟩-$CH_2$-$\underset{CH_3}{C}$=O | –$CH(CH_3)CH_2$–⟨⟩ |
| 50 | 21 | H | Cl | —$CH_2CH_3$ | Cl–⟨⟩–$CH_2$-$\underset{CH_3}{C}$=O | –$CH(CH_3)$–$CH_2$–⟨⟩–Cl |
| 51 | 21 | H | Cl | —$CH_3$ | ⟨⟩-$CH_2$-$\underset{CH_3}{C}$=O | –$CH(CH_3)CH_2$–⟨⟩ |
| 52 | 20 | H | —$CH_3$ | —$CH_3$ | $CH_3O$-(trimethoxyphenyl)-$CH_2$-$\underset{CH_3}{C}$=O | –$CH(CH_3)$–$CH_2$–(trimethoxyphenyl) |
| 53 | 22 | —$OCH_3$ | H | —$CH_2CH_3$ | ⟨⟩–$(CH_2)_2$–$\underset{CH_3}{C}$=O | –$CH(CH_3)$–$(CH_2)_2$–⟨⟩ |
| 54 | 21 | H | Cl | —$CH_3$ | $CH_3$—CHO | —$C_2H_5$ |
| 55 | 21 | H | Cl | —$CH_3$ | ⟨⟩-CHO | –$CH_2$–⟨⟩ |
| 56 | 21 | H | Cl | —$CH_3$ | ⟨⟩-$CH_2$-CHO | –$(CH_2)_2$–⟨⟩ |

The following examples illustrate the preparation of the 3,3-disubstituted-benzodioxepins I by forming the 3-spiro-2'-oxirane which when reacted with an amine gives the desired product I, that is the route D → E → I illustrated in Flow Diagram I. It will be appreciated that anyone of the intermediate compounds D described in this disclosure as well as others falling within the scoep of its definition can be employed as starting substance and any amine of structure $HNR^5R^6$ can be substituted for the particular amine employed to provide the desired product I.

EXAMPLE 57

3-Hydroxy-3-t.-butylaminomethyl-3,4-dihydro-2H-1,5-benzodioxepin hydrochloride

Step A: Preparation of 3,4-dihydro-2H-1,5-benzodioxepin-3-spiro-2'-oxirane

A solution of sodium nitrite (6.9 g.: 0.1 mole) in water (50 ml.) is added slowly over a period of ½ hour with stirring to a solution of 3-hydroxy-3-aminomethyl-3,4-dihydro-2H-1,5-benzodioxepin hydrochloride (23.17 g.; 0.1 mole), in water (200 ml.) containing acetic acid (0.1 ml.) while maintaining the reaction mixture at a temperature between about −4° to 0° C. When the addition is completed the reaction mixture then is allowed to warm to ambient temperature. The solid that forms is collected and washed with a little water to yield 14.84 g. of crude product, m.p. 132°–144° C. Following recrystallization from methanol (approximately 30 parts V/W) there is obtained 11.65 g. (65.38) of 3,4-dihydro-2H-1,5-benzodioxepin-3-spiro-2'-oxirane, m.p. 147°–149° C.

Analysis calculated for $C_{10}H_{10}O_3$: C, 67.40; H, 5.66; O, 26.94; Found: C, 67.46; H, 5.46; O, 27.37.

Recrystallization of the crude product of Step A from chloroform also provides purified product that does not depress the melting point when taken in admixture with the purified product of Step A.

The mother liquor remaining after the removal of the crude product in Step A is extracted with ether yielding an oil (1.3 g.) which crystallizes from carbon tetrachloride to afford 300 mgs. of 3-hydroxy-3-hydroxymethyl-3,4-dihydro-2H-1,5-benzodioxepin, M.P. 120°–123° C. Recrystallization of the diol from water (6 ml.) provides 254 mgs. of product, M.P. 124.5°–125.5° C.

Analysis calculated for $C_{10}H_{12}O_4$: C, 61.21; H, 6.17. Found: C, 61.16; H, 6.28.

The diol obtained as described above also exhibits β-adrenergic stimulating properties and therefore is useful as a bronchial dilating agent.

Step B.—Preparation of 3-hydroxy-3-t.-butylaminomethyl-3,4-dihydro-2H-1,5-benzodioxepin hydrochloride:

The 3,4-dihydro-2H-1,5-benzodioxepin-3-spiro-2'-oxirane (1.78 g.), obtained as described in Step A, is stirred at ambient temperature with t.-butylamine (3.2 ml.) in methanol (25 ml.) for 42 hours. The solution then is evaporated to 2.6 g. of oil which is separated and dissolved in ether and then acidified with 11N HCl in ethanol (2.5 ml.) to give 2.0 g. of crude product, m.p. 169.5°–177° C. After recrystallization from isopropanol containing decolorizing charcoal there is obtained 3-hydroxy-3-t.-butylaminomethyl-3,4-dihydro-2H-1,5-benzodioxepin hydrochloride, m.p. 186.5°–186.0° C.

Analysis calculated for $C_{14}H_{21}NO_3 \cdot HCl$: C, 58.43; H, 7.71; Cl, 12.32; N, 4.87; Found: C, 58.16; H, 7.62; Cl, 12.54; N, 5.04.

EXAMPLE 58

3-hydroxy-3-(2-dimethylaminoethyl)aminomethyl 2,4 dihydro-2H-1,5-benzodioxepin dihydrochloride 3,4-dihydro-2H-1,5-benzodioxepin-3-spiro-2'-oxirane (3.56 g., 20 millimoles) from Example 57, Step A, is stirred with 5.3 g. (60 millimoles) of unsymmetrical dimethylethylenediamine in 50 ml. of methanol for 48 hours at 30°–40° C. The solution is evaporated to remove methanol and excess dimethylethylenediamine. The residual oil is dissolved in diethyl ether and acidified with ethanolichydrogen chloride to give crude product hydrochloride. This product is dissolved in ethanol, treated with charcoal, and filtered. Concentration of the filtrate and refrigeration affords 3-hydroxy-3-(2-dimethylaminoethyl)aminomethyl-3,4-dihydro-2H-1,5-benzodioxepin dihydrochloride.

The following example describes the preparation of the 3-spiro-2'-oxirane E from a 3-oxo-benzodioxepin A employing a sulfur ylide. While the example describes the use of dimethyloxosulfonium methylide in the preparation of the 3-spiro-2'-oxirane, the desired oxirane can also be obtained by replacing the sulfur ylide by dimethylsulfonium methylide prepared in situ by the process heretofore described.

EXAMPLE 59

3,4-dihydro-2H-1,5-benzodioxepin-3-spiro-2'-oxirane

3-Oxo-3,4-dihydro-2H-1,5-benzodioxepin (1.64 g.; 10 millimoles) from Example 1, Step C, is added slowly with stirring during 15 minutes at ambient temperature to a solution of dimethyloxosulfonium methylide prepared under nitrogen from 15 millimoles of sodium hydride, 15 millimoles of trimethyloxosulfonium iodide, and 30 mls. of dimethyl sulfoxide. The mixture is stirred for 24 hours at ambient temperature and then 2 hours at 45°–50° C. The mixture is cooled and poured onto 50 g. of ice and repeatedly extracted with diethyl ether. The ethereal extract is washed with water, dried over anhydrous magnesium sulfate and evaporated. The crude product is crystallized from methanol to afford the 3,4-dihydro-2H-1,5-benzodioxepin-3-spiro-2'-oxirane identical with the product prepared from 3-hydroxy-3-aminomethyl-3,4-dihydro-2H-1,5-benzodioxepin as described in Example 57, Step A.

The other 3-oxo-3,4-dihydro-2H-1,5-benzodioxepins described specifically in this disclosure or falling within the scope of the definition of the 3-keto compound A can be substituted for the particular 3-keto starting substance in Example 59 to provide the desired 3-spiro-2'-oxirane of structure E.

Additional compounds prepared by the process described in Example 57 are identified in Table V. The products of Table V are prepared by replacing the t.-butylamine employed in Step B of Example 57 by an equimolecular quantity of the amine having the structure $HNR^5R^6$ identified in Table V and then following substantially the same procedure described in Step B.

TABLE V

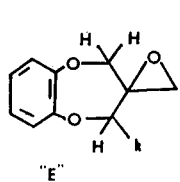 + HNR⁵R⁶ —Example 57 Step B Method→ 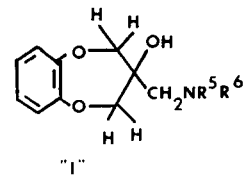

"E"  "I"

| Example No. | $-NR^5R^6$ | Empirical Formula | m.p. °C. | | C | H | Cl | N | S |
|---|---|---|---|---|---|---|---|---|---|
| 60 | $-NH-CH{<}^{CH_2}_{CH_2}$ | $C_{13}H_{17}NO_3 \cdot HCl$ | 187–189 | Calc. Found | 57.46 57.39 | 6.68 6.76 | 13.05 12.78 | 5.15 5.27 | |
| 61 | $-NH-C(CH_3)_2-C{\equiv}CH$ | $C_{15}H_{19}NO_3 \cdot HCl$ | 190.5–192.5 | Calc. Found | 60.50 60.25 | 6.77 6.86 | 11.91 12.04 | 4.70 4.88 | |
| 62 | $-N{\bigcirc}O$ (morpholino) | $C_{14}H_{19}NO_4 \cdot HCl$ | 173–176 | Calc. Found | 55.72 55.60 | 6.68 6.85 | 11.75 11.61 | 4.64 4.78 | |
| 63 | $-NH-C(CH_3)_2-CH_2OH$ | $C_{14}H_{21}NO_4 \cdot C_4H_4O_4$ | 138.5–140 | Calc. Found | 56.39 56.48 | 6.57 6.78 | | 3.65 3.77 | |
| 64 | $-N{\bigcirc}N-C_6H_5$ | $C_{20}H_{24}N_2O_3$ | 127–128 | Calc. Found | 70.57 70.81 | 7.11 7.44 | | 8.23 7.88 | |
| 65 | $-NH-pyridyl$ | $C_{15}H_{16}N_2O_3$ | | Calc. Found | | | | | |
| 66 | $-NH-adamantyl$ | $C_{20}H_{27}NO_3 \cdot HCl$ | 267–276 | Calc. Found | 65.65 66.04 | 7.71 7.87 | 9.69 9.86 | 3.83 4.09 | |
| 67 | $-NH-(CH_2)_2-O-(CH_2)_2-OH$ | $C_{14}H_{21}NO \cdot HCl$ | 157–158.5 | Calc. Found | 52.58 52.26 | 6.93 6.53 | 11.09 11.42 | 4.38 4.30 | |
| 68 | $-NH-(CH_2)_3-N{\bigcirc}O$ | $C_{17}H_{26}N_2O_4 \cdot 2HCl$ | 270–281 | Calc. Found | 51.65 51.88 | 7.14 7.52 | 17.94 17.64 | 7.09 6.85 | |
| 69 | $-NH-CH_2-CHOH-CH_2-$thiadiazolyl | $C_{15}H_{19}N_3O_5S \cdot C_2H_2O_4$ | 177–180 | Calc. Found | 46.05 46.18 | 4.77 5.10 | | 9.48 9.53 | 7.23 7.52 |
| 70 | $-NH-C_6H_5$ | $C_{16}H_{17}NO_3 \cdot HCl$ | 190–195 | Calc. Found | 62.44 62.40 | 5.89 5.99 | 11.52 11.75 | 4.55 4.37 | |
| 71 | $-NH(CH_2)_6NH-CH_2$-benzodioxepin-OH [1] | $C_{26}H_{36}N_2O_6 \cdot 2HCl$ | 274–277 | Calc. Found | 57.25 57.15 | 7.02 7.02 | 13.00 13.26 | 5.14 5.32 | |
| 72 | $-NHCH_2CH(OH)-C_6H_5$ | $C_{18}H_{21}NO_4 \cdot HCl$ | 200–202 | Calc. Found | 61.45 61.65 | 6.30 6.50 | 10.08 10.32 | 3.98 3.90 | |
| 72-a | $-NH-$cyclohexyl-$C_6H_5 \cdot HCl$ | $C_{22}H_{27}NO_3 \cdot HCl$ | 213.5–2.5.0 | Calc. Found | 67.77 67.92 | 7.24 7.40 | 9.09 9.55 | 3.59 3.58 | |

[1] 2 mole of epoxide to 1 mole of the diamine employed in synthesis.

Additional 3,3-disubstituted-benzodioxepins made by the reaction of 3,4-dihydro-2H-1,5-benzodioxepin-3-spiro-2'-oxirane and an amine of the structure HNR⁵R⁶ by the process described in Example 57, Step B, are described in Table VI.

TABLE VI

[Reaction scheme: benzodioxepin-spiro-oxirane + HNR⁵R⁶ → (Example 57 Step B Method) → 3-hydroxy-3-(CH₂NR⁵R⁶)-benzodioxepin]

| Ex. No. | R⁵ | R⁶ |
|---|---|---|
| 73 | H | —C₆H₄—Cl |
| 74 | H | —C₆H₄—CH₃ |
| 75 | H | —C₆H₄—OCH₃ |
| 76 | —(CH₂)₂—N(H)—(CH₂)₂— (cyclic) | |
| 77 | —(CH₂)₂—N(CH₃)—(CH₂)₂— (cyclic) | |
| 78 | H | —CH₂—CH=CH₂ |
| 79 | H | —CH₂—C(CH₃)=CH₂ |
| 80 | H | —CH(CH₃)₂ |
| 81 | H | —CH(CH₃)—CH₂—C₆H₄—OH |
| 82 | H | —CH(CH₃)—CH₂—(indol-3-yl) |
| 83 | H | —CH(CH₃)—CH₂—C₆H₅ |
| 84 | H | —CH₂(CH₂)₅NH₂ |

The following examples describe the preparation of certain 3,3-disubstituted-benzodioxepins having at least one substituent attached to its benzenoid moiety.

EXAMPLE 85

3-Hydroxy-3-isopropylaminomethyl-7-nitro-3,4-dihydro-2H-1,5-benzodioxepin Hydrochloride

Step A.—Preparation of 7-Nitro-3,4-dihydro-2H-1,5-benzodioxepin-3-spiro-2'-oxirane:

A mixture of 0.11 mole of nitronium tetrafluoroborate and 60 g. tetramethylene sulfone is stirred at 10°C. and 0.1 mole of 3,4-dihydro-2H-1,5-benzodioxepin-3-spiro-2'-oxirane, prepared as described in Example 57, Step A, added during 30 minutes. The cooling bath then is removed and the mixture stirred an additional 20 minutes at 35° C., poured into ice and water, the product extracted with ether, the ether solution dried over magnesium sulfate and evaporated. The product obtained following crystallization from a mixture of chloroform and petroleum ether is 7-nitro-3,4-dihydro-2H-1,5-benzodioxepin-3-spiro-2'-oxirane.

Step B: Preparation of 3-hydroxy-3-isopropylaminomethyl-7-nitro-3,4-dihydro-2H-1,5-benzodioxepin Hydrochloride By replacing the 3-spiro-2'-oxirane and the t.-butylamine employed in Step B of Example 57 by equivalent quantities of 7-nitro-3,4-dihydro-2H-1,5-benzodioxepin-3-spiro-2'-oxirane and isopropylamine respectively and then following substantially the same procedure there described, there is obtained 3-hydroxy-3-isopropylaminomethyl-7-nitro-3,4-dihydro-2H-1,5-benzodioxepin hydrochloride.

EXAMPLE 86

3-Hydroxy-3-isopropylaminomethyl-7-amino-3,4-dihydro-2H-1,5-benzodioxepin Hydrochloride

Step A.—Preparation of 3-Acetoxy-3-(N-acetylisopropylaminomethyl)-7-nitro-3,4-dihydro-2H-1,5-benzodioxepin:

Treatment of 3-hydroxy-3-isopropylaminomethyl-7-nitro-3,4-dihydro-2H-1,5-benzodioxepin, obtained as described in Example 85, with excess acetic anhydride and heating overnight on a water bath affords the 3-acetoxy-3-(N-acetylisopropylaminomethyl)-7-nitro-3,4-dihydro-2H-1,5-benzodioxepin.

Step B.—Preparation of 3-Acetoxy-3-(N-acetylisopropylaminomethyl)-7-amino-3,4-dihydro-2H-1,5-benzodioxepin:

The 3-acetoxy-3-(N-acetylisopropylaminomethyl)-7-nitro-3,4-dihydro-2H-1,5-benzodioxepin when dissolved in ethyl acetate is reduced at low pressure over platinum with hydrogen to give 3-acetoxy-3-(N-acetylisopropylaminomethyl)-7-amino-3,4-dihydro-2H-1,5-benzodioxepin.

Step C.—3-Hydroxy-3-(isopropylaminomethyl)-7-amino-3,4-dihydro-2H-1,5-benzodioxepin hydrochloride:

3-Acetoxy-3-(N-acetylisopropylaminomethyl)-7-amino-3,4-dihydro-2H-1,5-benzodioxepin (33.6 g., 0.1 mole) is refluxed for 10 hours with 400 ml. of methanol containing 20 g. (0.5 mole) of sodium hydroxide. The solvent is removed at low temperature in vacuo and the residue treated with 200 ml. of water. The mixture is extracted with diethyl ether and the combined ethanol phases washed with water and dried over anhydrous magnesium sulfate. The solvent is evaporated and the product, 3-hydroxy-3-(isopropylaminomethyl)-7-amino-3,4-dihydro-2H-1,5-benzodioxepin hydrochloride isolated as the hydrochloride salt.

EXAMPLE 87

3-Hydroxy-3-isopropylaminomethyl-7-methanesulfonamido-3,4-dihydro-2H-1,5-benzodioxepin Hydrochloride

Step A.—Preparation of 3-Acetoxy-3-(N-acetylisopropylaminomethyl)-7-methanesulfonamido-3,4-dihydro-2H-1,5-benzodioxepin:

Methanesulfonyl chloride (0.1 mole) is added dropwise to a stirred solution of 0.1 mole of 3-acetoxy-3-(N-acetoxyisopropylaminomethyl)-7-amino-3,4-dihydro- 2H-1,5-benzodioxepin, from Example 86, Step B, in 120 ml. of pyridine held at 10°–15°C. The mixture is stirred for several hours at ambient temperature, then heated to 90°C. for 0.5 hours, cooled, and added to an ice-water mixture. The mixture is extracted with ether, washed, dried over magnesium sulfate, and the solvent removed to give 3-acetoxy-3-(N-acetylisopropylaminomethyl)-7-methanesulfonamido-3,4-dihydro-2H-1,5-benzodioxepin.

Step B.—Preparation of 3-Hydroxy-3-isopropylaminomethyl-7-methanesulfonamido-3,4-dihydro-2H-1,5-benzodioxepin:

3-Acetoxy-3-(N-acetylisopropylaminomethyl)-7-methanesulfonamido-3,4-dihydro-2H-1,5-benzodioxepin (4.2 g., 10 millimole) in 20 ml. methanol is treated with 2 g. (50 millimoles) of sodium hydroxide in 20 ml. of methanol. The mixture is refluxed for 3 hours, cooled, and diluted with 400 mls. of water, neutralized with acid and extracted with ether. The combined ethereal solutions are washed with water, dried over anhydrous sodium sulfate, and evaporated to give 3-hydroxy-3-isopropylaminomethyl-7-methanesulfonamido-3,4-dihydro-2H-1,5-benzodioxepin.

EXAMPLE 88

3-Hydroxy-3-isopropylamino-7-carbethoxyamine-3,4-dihydro-2H-1,5-benzodioxepin

Step A.—Preparation of 3-Acetoxy-3-(N-acetylisopropylaminomethyl)-7-carbethoxyamine-3,4-dihydro-2H-1,5-benzodioxepin:

3-Acetoxy-3-N-acetylisopropylaminomethyl-7-amino-3,4-dihydro-2H-1,5-benzodioxepin (0.1 mole) from Example 86, Step B, in chloroform is treated with 0.11 mole of ethyl chloroformate and pyridine in chloroform. The mixture after stirring and heating in a water bath for several hours is diluted with water, extracted with ether, the combined ethereal extracts washed, dried and evaporated to give 3-acetoxy-3-(N-acetylisopropylaminomethyl)-7-carbethoxyamino-3,4-dihydro-2H-1,5-benzodioxepin.

Step B.—Preparation of 3-Hydroxy-3-isopropylaminomethyl-7-carbethoxyamino-3,4-dihydro-2H-1,5-benzodioxepin:

3-Acetoxy-3-(N-acetylisopropylaminomethyl)-7-carbethoxyamino-3,4-dihydro-2H-1,5-benzodioxepin (4.1 g., 10 millimoles) is warmed five hours at 40°C. with 6 ml. of concentrated hydrochloric acid and 34 ml. of ethanol. The solution is cooled, taken to the basic side with sodium hydroxide, diluted with water, and extracted with diethyl ether to give 3-hydroxy-3-isopropylaminomethyl-7-carbethoxyamino-3,4-dihydro-2H-1,5-benzodioxepin.

EXAMPLE 89

3,7-Dihydroxy-3-isopropylaminomethyl-3,4-dihydro-2H-1,5-benzodioxepin

3-Acetoxy-3-(N-acetylisopropylaminomethyl-7-amino-3,4-dihydro-2H-1,5-benzodioxepin from Example 86, Step B, dissolved in dilute sulfuric acid is treated with sodium nitrite in water and the mixture heated on a water bath for 0.5 hours. The mixture is cooled, neutralized with base, extracted with ether, the ethereal extract washed, dried, and evaporated to give 3,7-dihydroxy-3-isopropylaminomethyl-3,4-dihydro-2H-1,5-benzodioxepin.

EXAMPLE 90

3-Hydroxy-3-isopropylaminomethyl-7-methoxy-3,4-dihydro-2H-1,5-benzodioxepin 3,7-Dihydroxy-3-isopropylaminomethyl-3,4-dihydro-2H-1,5-benzodioxepin (2.53 g.; 10 millimoles) from Example 89 dissolved in 50 ml. of diethyl ether is left 10 hours at ambient temperature with 0.46 g. (11 millimoles) of diazomethane in 25 ml. of diethyl ether. Excess diazomethane is destroyed by addition of a few drops of acetic acid. The solution then is washed with water, dried over anhydrous sodium sulfate, and evaporated to dryness to give 3-hydroxy-3-isopropylaminomethyl-7-methoxy-3,4-dihydro-2H-1,5-benzodioxepin.

The products of Examples 85 through 90 can also be prepared following substantially the same procedures described in these examples but instead of employing the 3-spiro-2'-oxirane starting substances in Example 85, Step A, one uses an oxarolidinone which can be prepared from product I by treatment with dibutyl carbonate and metallic sodium or by treatment with phosgene. The following example illustrates the preparation of the oxazolidinone and its use in preparing the desired 7-substituted compounds of Examples 85 through 90.

EXAMPLE 91

3-Hydroxy-3-isopropylaminomethyl-7-nitro-3,4-dihydro-2H-1,5-benzodioxepin.

Step A.—Preparation of 3'-isopropyl-3,4-dihydro-2H-1,5-benzodioxepin-3-spiro-5'-oxazolidin-2'-one:

A mixture of 3-hydroxy-3-isopropylaminomethyl-3,4-dihydro-2H-1,5-benzodioxepin (11.85 g.; 50 millimoles), prepared as described in Example 1, and dibutyl carbonate (13.1 g.) with a small piece of metallic sodium is heated in an oil bath. The temperature then is slowly raised to 170° C. with removal of butanol. Finally, the mixture is heated between 170°–200° C. with removal of excess dibutyl carbonate. The cooled reaction product is dissolved in benzene, washed with water, dried over sodium sulfate, and the solvent evaporated to give 3'-isopropyl-3,4-dihydro-2H-1,5-benzodioxepin-3-spiro-5'-oxazolidin-2'-one, m.p. 121°–122° C.

Step B.—Preparation of 3'-isopropyl-7-nitro-3,4-dihydro-2H-1,5-benzodioxepin-3-spiro-5'-oxazolidin-2'-one:

By replacing the 3,4-dihydro-2H-1,5-benzodioxepin-3-spiro-2'-oxirane employed in Example 85, Step A, by a equivalent amount of 3'-isopropyl-3,4-dihydro-2H-1,5-benzodioxepin-3-spiro-5'-oxazolidin-2'-one and following substantially the same procedure there described, there is obtained 3'-isopropyl-7-nitro-3,4-dihydro-2H-1,5-benzodioxepin-3-spiro-5'-oxazolidin-2'-one, m.p. 145.5°–147° C.

Step C.—Preparation of 3-hydroxy-3-isopropylaminomethyl-7-nitro-3,4-dihydro-2H-1,5-benzodioxepin:

A mixture of 0.15 mole of the oxazolidinone from Step B above and 15 g. (0.38 mole) of sodium hydroxide in 100 ml. of water and 200 ml. of 95% ethanol is refluxed, the solution evaporated to a small volume and the product extracted with diethyl ether. Evaporation of the solvent gives 3-hydroxy-3-isopropylaminomethyl-7-nitro-3,4-dihydro-2H-1,5-benzodioxepin.

EXAMPLE 92

3-Hydroxy-3-isopropylaminomethyl-7-methanesulfonamido-3,4-dihydro-2H-1,5-benzodioxepin

Step A.—Preparation of 3'-isopropyl-7-amino-3,4-dihydro-2H-1,5-benzodioxepin-3-spiro-5'-oxazolidin-2'-one:

By replacing the 3-acetoxy-3-N-acetylisopropylaminomethyl-7-nitro-3,4-dihydro-2H-1,5-benzodioxepin used in Example 86, Step B, by an equivalent quantity of 3'-isopropyl-7-nitro-3,4-dihydro-2H-1,5-benzodioxepin-3-spiro-5'-oxazolidin-2'-one obtained as described in Example 91, Step B, and then following substantially the procedure described in Example 86, Step B, there is obtained 3'-isopropyl-7-amino-3,4-dihydro-2H-1,5-benzodioxepin-3-spiro-5'-oxazolidin-2'-one.

Step B.—Preparation of 3'-isopropyl-7-methanesulfonamido-3,4-dihydro-2H-1,5-benzodioxepin-3-spiro-5'-oxazolidin-2'-one:

By reacting the oxazolidinone obtained in Step A with methanesulfonyl chloride and employing the other reaction conditions and procedure described in Example 87, Step A, there is obtained 3'-isopropyl-7-methanesulfonamido-3,4-dihydro-2H-1,5-benzodioxepin-3-spiro-5'-oxazolidin-2'-one.

Step C.—Preparation of 3-hydroxy-3-isopropylaminomethyl-7-methanesulfonamido-3,4-dihydro-2H-1,5-benzodioxepin:

This product is prepared by substituting the oxazolidinone compound of Step B above for that employed in Example 91, Step C, and following essentially the same reaction there described.

EXAMPLE 93

3-Hydroxy-3-isopropylaminomethyl-7-carbethoxyamino-3,4-dihydro-2H-1,5-benzodioxepin

Step A.—Preparation of 3'-isopropyl-7-ethoxycarbonylamino-3,4-dihydro-2H-1,5-benzodioxepin-3-spiro-5'-oxazolidin-2'-one:

By replacing the 3-acetoxy-3-N-acetyliospropylamino-7-amino-3,4-dihydro-2H-1,5-benzodioxepin reactant in Example 88, Step A, by the 5'-isopropyl-7-amino-3,4-dihydro-2H-1,5-benzodioxepin-3-Spiro-5-oxazolidin-2'-one, prepared as described in Example 92, Step A, and then following substantially the same procedure described in Example 88, Step A, there is obtained 3'-isopropyl-7-carbethoxyamino-3,4-dihydro-2H-1,5-benzodioxepin-3-spiro-5'-oxazolidin-2'-one.

Step B.—Preparation of 3-hydroxy-3-isopropylaminomethyl-7-carbethoxyamino-3,4-dihydro-2H-1,5-benzodioxepin:

This oxazolidinone from Step A above is refluxed in ethanol containing anhydrous hydrogen chloride. The solution is neutralized, evaporated to a small volume, diluted with water and extracted with ether. The dried etheral solution is evaporated to give the desired product.

EXAMPLE 94

3,7-Dihydroxy-3-isopropylaminomethyl-3,4-dihydro-2H-1,5-benzodioxepin

Step A.—Preparation of 3'-isopropyl-7-hydroxy-3,4-dihydro-2H-1,5-benzodioxepin-3-spiro-5'-oxazolidin-2'-one:

This product is prepared by following the procedure and employing the reactants and reaction conditions described in Example 89 except the 3-acetoxy-3-N-acetylisopropylaminomethyl-7-amino-3,4-dihydro-2H-1,5-benzodioxepin there employed is replaced by the oxazolidinone obtained as described in Example 92, Step A.

Step B.—Preparation of 3,7-dihydroxy-3-isopropylaminomethyl-3,4-dihydro-2H-1,5-benzodioxepin:

This product is prepared by substituting the oxazolidinone compound of Step A above for that employed in Example 91, Step C, and following essentially the same reaction there described.

EXAMPLE 95

3-Hydroxy-3-isopropylaminomethyl-7-methoxy-3,4-dihydro-2H-1,5-benzodioxepin

Step A.—Preparation of 3'-isopropyl-7-methoxy-3,4-dihydro-2H-1,5-benzodioxepin-3-spiro-5'-oxazolidin-2'-one:

This compound is prepared by employing the same reactants, reaction conditions and procedure outlined in Example 90 except the 3,7-dihydroxy-3-isopropylaminomethyl-3,4-dihydro-2H-1,5-benzodioxepin is replaced by an equivalent quantity of 3'-isopropyl-7-hydroxy-3,4-dihydro-2H-1,5-benzodioxepin-3-spiro-5'-oxazolidin-2'-one from Example 94, Step A.

Step B.—Preparation of 3-hydroxy-3-isopropylaminomethyl-7-methoxy-3,4-dihydro-2H-1,5-benzodioxepin:

This product is prepared by substituting the oxazolidinone compound of Step A above for that employed in Example 91, Step C, and following essentially the same reaction there described.

EXAMPLE 96

3,6-Dihydroxy-3-isopropylaminomethyl-3,4-dihydro-2H-1,5-benzodioxepin Hydrochloride

Step A.—Preparation of 2-methoxy-2-methyl-4-hydroxy-1,3-benzodioxole:

A mixture of pyrogallol (25.2 g., 0.2 mole) and trimethyl orthoacetate (26.4 g., 0.22 mole) is treated with one drop of concentrated sulfuric acid and the reaction mixture then stirred under nitrogen in an oil bath at 103°–105° C. Methanol formed in the reaction is distilled up a short column and collected. After 1 hour, more trimethyl orthoacetate (2 g., 0.016 mole) and another drop of sulfuric acid are added and the temperature of the oil bath raised to 108°–110° C. for a further hour. Methanol (9.6 ml.) is collected. On cooling, the dark brown oil crystallizes and is dissolved in ether (120 dissolved the ethereal solution is washed with 2% sodium carbonate solution (50 ml.) and then with saturated sodium chloride solution. Evaporation of the dried ethereal solution yields 31.2 g. of a pale yellow solid. The crude product is dissolved in boiling carbon tetrachloride (280 ml.) and some solid (mainly pyrogallol) is removed by filtration. On cooling, the solution yields 24.24 g. (66.6%) of 2-methoxy-2-methyl-4-hydroxy-1,3-benzodioxole, m.p. 106°–109° C. Upon further recrystallization of the compound from carbon tetrachloride, with treatment with charcoal and activated alumina, the product melts at 114.5°–115.5° C.

Analysis calculated for $C_9H_{10}O_4$: C, 59.33; H, 5.53. Found: C, 59.70; H, 5.83.

Step B.—Preparation of 2-Methoxy-2-methyl-4-benzyloxy-1,3-benzodioxole;

To a suspension of sodium hydride (2.4 g., 0.1 mole) in freshly distilled hexamethyl-phosphoramide (24 ml.) is added dropwise with stirring under dry nitrogen a solution of 2-methoxy-2-methyl-4-hydroxy-1,3-benzodioxole (18.2 g., 0.1 mole) in hexamethylphosphoramide (36 ml.) and stirring is continued at ambient temperature until hydrogen evolution essentially ceases. Benzyl chloride (12.65 g., 0.1 mole) is added and the mixture stirred at 75°–80° C. for 5 hours. The mixture then is poured onto ice and adjusted to ca. pH 6 with acetic acid. The product is extracted with ether, and the ethereal solution washed with 2% sodium carbonate solution (50 ml.) and then with saturated sodium chloride solution. After drying over magnesium sulphate and then calcium sulfate, the ethereal solution is evaporated to give 2-methoxy-2-methyl-4-benzyloxy-1,3-benzodioxole which can be crystallized from di-isopropyl ether.

Step C.—Preparation of 3-benzyloxy catechol:

A mixture of 2-methoxy-2-methyl-4-benzyloxy-1,3-benzodioxole (13.6 g., 0.05 mole), methanol (210 ml.) and 5N hydrochloric acid (210 ml.) is stirred under reflux in an atmosphere of nitrogen for 10 hours. Most of the methanol is distilled off under vacuum and the product then extracted with ether. The ethereal solution is washed with water, dried over magnesium sulfate followed by calcium sulfate and evaporated to dryness to yield the crude 3-benzyloxy-catechol which can be recrystallized from di-isopropyl ether.

Step D.—Preparation of 3-amino-4-cyano-6-benzyloxy-3,4-dihydro-2H-1,5-benzodioxepin:

By replacing catechol employed in Step A of Example 1 by an equivalent quantity of 3-benzyloxycatechol and following substantially the same procedures described in Steps A and B of Example 1 there are obtained sequentially 1,2-di(cyanomethoxy)-3-benzyloxybenzene and then 3-amino-4-cyano-6-benzyloxy-3,4-dihydro-2H-1,5-benzodioxepin and/or the 9-benzyloxy isomer.

Step E.—Preparation of 3,6-dihydroxy-3-isopropylaminomethyl-3,4-dihydro-2H-1,5-benzodioxepin hydrochloride:

The 3-amino-4-cyano-6-benzyloxy-3,4-dihydro-2H-1,5-benzodioxepin and/or its 9-benzyloxy isomer is converted to 3-oxo-6-benzyloxy-3,4-dihydro-2H-1,5-benzodioxepin by the procedure described in Example 1, Step C, and the 3-keto compound then reacted with potassium cyanide by either the process of Step D of Example 1 or the alternative procedure there described to provide 3-hydroxy-3-cyano-6-benzyloxy-3,4-dihydro-2H-1,5-benzodioxepin. This product then is reduced with lithium aluminum hydride by the method outlined in the alternate of Step E, Example 1, to give 3-hydroxy-3-aminomethyl-6-benzyloxy-3,4-dihydro-2H-1,5-benzodioxepin which when reacted with acetone and then reduced by the process of Step F, Example 1, there is obtained 3,6-dihydroxy-3-isopropylaminomethyl-3,4-dihydro-2H-1,5-benzodioxepin hydrochloride.

Additional 3,3-disubstituted-benzodioxepins having at least one substituent attached to the benzenoid moiety that can be prepared from the appropriate catechol by any of the major routes illustrated in Flow Diagram II followed by any of the procedures illustrated in Flow Diagram I are identified in the following Table. For convenience the catechols identified in Table VII are converted to the 3-oxo-benzodioxepin by substantially the same methods described in Example 1, Steps A through C (that is route E → $F^1$ → $G^1$ → A in Flow Diagram II). The other route (that is E → $F^2$ → $G^2$ → A) described in Examples 108 and 109 could have been employed to provide the 3-oxo-benzodioxepin A and the following table is to be understood as applying to this route as well. Also, for convenience the end products I are prepared by the procedures described in Examples 1, Steps D through F, Example 23 or Example 57, as indicated in the table (that is route A → C → D → I; A → B → D → I, and A → C → D → E → I) although the other modifications illustrated in Flow Diagram I and in the Examples could equally be employed.

TABLE VII

| Ex. No. | R | $R^1$ | X | $R^4$ | $R^3$ | $R^6$ | Ex. No. | Steps |
|---|---|---|---|---|---|---|---|---|
| 97 | H | $(CH_3)_3C-$ | H | H | H | $-CH(CH_3)_2$ | 1 | D-F |
| 98 | H | $(CH_3)_3C-$ | $CH_3$ | H | H | $-CH(CH_3)_2$ | 57 | A-B |
| 99 | H | $(CH_3)_3C-$ | $(CH_3)_3C-$ | H | (pyridyl) | $-CH(CH_3)_2$ | 123 | C |

TABLE VII-continued

| Ex. No. | R | R¹ | X | R⁴ | R³ | R⁶ | Method For A-I Ex. No. | Steps |
|---|---|---|---|---|---|---|---|---|
| 100 | H | $(CH_3)_2CH-$ | $(CH_3)_2CH-$ | H | H | $-C(CH_3)_3$ | 57 | A-B |
| 101 | $(CH_3)_2CH-$ | H | $(CH_3)_2CH-$ | H | H | $-CH(CH_3)_2$ | 1 | D-F |
| 102 | $(CH_3)_2CH-$ | H | H | $CH_3$ | H | $-\overset{CH_3}{CH}-CH_2-\langle\!\!\!\!\bigcirc\!\!\!\!\rangle$ | 23 | A-C |
| 103 | H | $(CH_3)_2CH$ | H | H | H | $-C(CH_3)_3$ | 57 | A-B |
| 104 | $CH_3O-$ | H | H | $-CH_2CH_3$ | H | $-\overset{CH_3}{CH}-CH_2-\langle\!\!\!\!\bigcirc\!\!\!\!\rangle-OH$ | 24 | A-B |
| 105 | $CH_3-$ | H | H | H | $\langle\!\!\!\!\overset{N}{\bigcirc}\!\!\!\!\rangle-CH_2-$ | $-CH(CH_3)_2$ | 123 | C |
| 106 | H | $CH_3-$ | H | H | H | $-C(CH_3)_3$ | 57 | A-B |
| 107 | H | $NO_2$ | H | H | H | $-\overset{CH_3}{CH}-CH_2-\langle\!\!\!\!\overset{}{\underset{N}{\bigcirc}}\!\!\!\!\rangle$ | 57 | A-B |

EXAMPLE 108

3-Hydroxy-3-isopropylaminomethyl-3,4-dihydro-2H-1,5-benzodioxepin Hydrochloride

Step A.—Preparation of 1,2-bis-carbomethoxymethoxybenzene (or 1,2-benzene-bis methyl glycolate):

Methyl bromoacetate (57 g.) is added portionwise to a mixture of catechol (24 g.), potassium carbonate (62 g.), potassium iodide (3 g.) and acetone (500 ml.). The reaction gradually warmed up and a precipitate formed. The reaction mixture then was stirred overnight at ambient temperature and the precipitated substance removed by filtration. The acetone solution was distilled to remove the acetone whereupon an oily residue was obtained which was crystallized from methanol yielding 27 g. of 1,2-bis-carbomethoxymethoxybenzene.

Step B: Preparation of 3-oxo-4-carbomethoxy-3,4-dihydro-2H-1,5-benzodioxepin.

Potassium t.-butoxide (15.8 g.) dissolved in DMSO (130 ml.) is added dropwise over a 45 minute period to 1,2-bis-carbomethoxymethoxybenzene (18.3 g.) in DMSO (30 ml.) under an atmosphere of nitrogen. The mixture then is stirred 3 hours at ambient temperature and a mixture of acetic acid (16 ml.) and water (200 ml.) is added. The reaction mixture is extracted with benzene, the powdery material removed by filtration and the benzene then dried over magnesium sulfate and the benzene then evaporated leaving 3-oxo-4-carbomethoxy-3,4-dihydro-2H-1,5-benzodioxepin that is used in the following step without purification.

Step C: Preparation of 3-oxo-3,4-dihydro-2H-1,5-benzodioxpin.

3-Oxo-4-carbomethoxy-3,4-dihydro-2H-1,5-benzodioxepin (110 g.) is added to a mixture of methanol (210 ml.), concentrated hydrochloric acid (50 ml.) and water (160 ml.) and the mixture then is refluxed for 18 hours. The product is extracted with ether, and the ether extract washed with four 50 ml. portions of sodium bicarbonate solution, then twice with 50 ml. portions of water. After drying the washed ether extract over magnesium sulfate and evaporation to remove the solvent there is obtained 3-oxo-3,4-dihydro-2H-1,5-benzodioxepin.

Step D: Preparation of 3-hydroxy-3-isopropylaminomethyl-3,4-dihydro-2H-1,5-benzodioxepin hydrochloride The 3-oxo-3,4-dihydro-2H-1,5-benzodioxepin is converted to the desired 3-hydroxy-3-isopropylaminomethyl-3,4-dihydro-2H-1,5-benzodioxepin hydrochloride by the procedures described in Example 1.

EXAMPLE 109

2-(2-Pyridyl)-3-hydroxy-3-isopropylaminomethyl-3,4-dihydro-2H-1,5-benzodioxepin hydrochloride.

Step A: Preparation of 2-(2-Pyridyl)-2-(2-carboxymethoxyphenoxy)-acetic acid.

A mixture of 2-hydroxyphenoxy acetic acid (16.8 g. 0.1 mole) and 80 ml. of 5N aqueous sodium hydroxide (0.4 mole) is stirred until solution is effected, then the solution treated with 2-bromo-2-(2-pyridyl)-acetic acid (21.6 g. 0.1 mole), and refluxed for 20 hours. The cooled solution is taken to neutrality and the diacid crystallized from benzene to give 2-(2-pyridyl)-2-(carboxymethoxyphenoxy)-acetic acid.

Step B: Preparation of methyl 2-(2-pyridyl)-2-(2-carbomethoxymethoxyphenoxy)-acetate.

A solution of the above diacid (30.3 g. 0.1 mole) p-toluenesulfonic acid (3 g.) and 300 mls. of methanol is refluxed for twenty-four hours and the solvent then removed, and replaced by diethyl ether. The ethereal solution is washed with water, 5% sodium bicarbonate, then again with water, dried over anhydrous sodium sulfate, and evaporated to give methyl 2-(2-pyridyl)-2-(2-carbomethoxymethoxyphenoxy) acetate.

Step C.—Preparation of 2-(2-pyridyl)-3-oxo-3,4-dihydro-2H-1,5-benzodioxepin:

By following substantially the same procedure described in Example 108, Steps B and C, but substituting methyl 2-(2-pyridyl)-2-(2-carbomethoxymethoxyphenoxy)-acetate for the 1,2-bis-(carbomethoxymethoxy)benzene there is obtained sequentially 2-(2-pyridyl)-3-oxo-4-carbomethoxy-3,4-dihydro-2H-1,5-benzodioxepin and then 2-(2-pyridyl)-3-oxo-3,4-dihydro-2H-1,5-benzodioxepin.

Step D.—Preparation of 2-(2-pyridyl)-3-hydroxy-3-isopropylaminomethyl-3,4-dihydro-2H-1,5-benzodioxpin hydrochloride:

This product is prepared by replacing the 3-oxobenzodioxepin employed in Example 1, Step D, by an equivalent quantity of 2-(2-pyridyl)-3-oxo-3,4-dihydro-2H-1,5-benzodioxepin and then employing the other reactants and reaction conditions of Steps D through F of Example 1.

Other compounds exemplary of those that can be prepared by the processes called for in Example 109 are identified in Table VIII. These 2-substituted-benzodioxepins are made by replacing the 2-bromo-2-(2-pyridyl)-acetic acid employed in Step A of Example 109 by an equivalent quantity of the haloacetic acid identified in the following table and then following the procedures of Example 109 Steps A and B, Example 108, Steps B and C and finally Steps D through F of

TABLE VIII

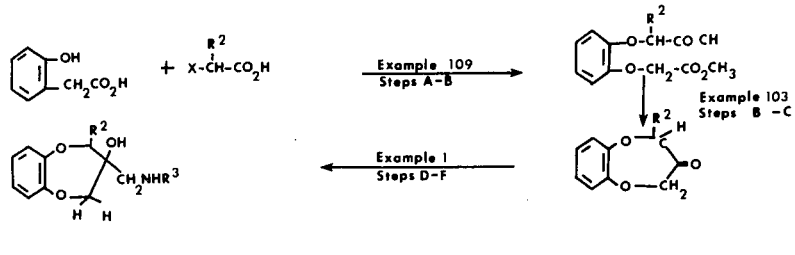

| Ex. No. | X | $R^2$ | Carbonyl Reactant | $R^6$ |
|---|---|---|---|---|
| 110 | Br | (pyridyl-N)-CH$_2$- | (CH$_3$)$_2$C=O | —CH(CH$_3$)$_2$ |
| 111 | Br | (cyclohexyl H)— | (CH$_3$)$_2$C=O | —CH(CH$_3$)$_2$ |
| 112 | Br | (phenyl)— | (CH$_3$)$_2$C=O | —CH(CH$_3$)$_2$ |
| 113 | Cl | CH$_3$CH$_2$— | (CH$_3$)$_2$C=O | —CH(CH$_3$)$_2$ |
| 114 | Br | | HO-(phenyl)-CH$_2$-C(CH$_3$)=O | -CH(CH$_3$)CH$_2$-(phenyl) |
| 115 | Br | (phenyl) | HO-(phenyl)-CH$_2$-C(CH$_3$)=O | -CH(CH$_3$)-CH$_2$-(phenyl)-OH |
| 116 | Cl | CH$_3$CH$_2$— | HO-(phenyl)-CH$_2$-C(CH$_3$)=O | -CH(CH$_3$)-CH$_2$-(phenyl)-OH |
| 117 | Br | (pyridyl-N)-CH$_2$- | (indolyl)-CH$_2$-C(CH$_3$)=O | -CH(CH$_3$)-CH$_2$-(indolyl) |
| 118 | Br | (cyclohexyl H)— | (indolyl)-CH$_2$-C(CH$_3$)=O | -CH(CH$_3$)-CH$_2$-(indolyl) |

TABLE VIII-continued

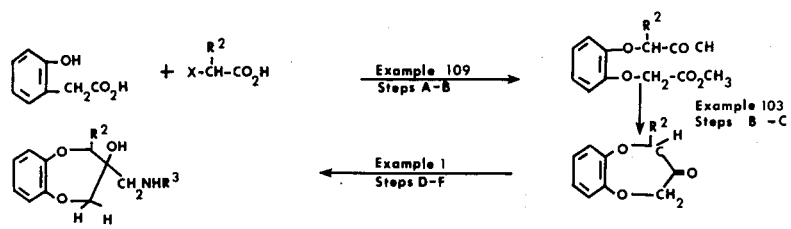

| Ex. No. | X | R² | Carbonyl Reactant | R⁶ |
|---------|---|----|--------------------|-----|
| 119 | Br | –C₆H₅ | indolyl-CH₂-C(CH₃)=O | -CH(CH₃)-CH₂-indolyl |
| 120 | Cl | CH₃CH₂— | C₆H₅-CH₂-C(CH₃)=O | -CH(CH₃)CH₂-C₆H₅ |
| 121 | Br | pyridyl | C₆H₅-CH₂-C(CH₃)=O | -CH(CH₃)CH₂-C₆H₅ |
| 122 | Br | C₆H₅ | C₆H₅-CH₂-C(CH₃)=O | -CH(CH₃)CH₂-C₆H₅ |

EXAMPLE 123

2-Phenyl-3-hydroxy-3-isopropylaminomethyl-3,4-dihydro-2H-1,5-benzodioxepin hydrochloride

Step A. Preparation of 2-(2-hydroxyphenoxy)acetonitrile

A mixture of catechol (11 g., 0.1 mole), chloroacetonitrile (5.3 g., 0.07 mole), finely powdered potassium carbonate (11.1 g., 0.08 mole) and acetone (75 ml.) is refluxed with stirring for 2 hours. The mixture then is treated with chloroacetonitrile (3.8 g., 0.05 mole) and potassium carbonate (7.6 g., 0.055 mole) and refluxed for 4 hours. The mixture is filtered, the solids washed with more acetone and the combined filtrate evaporated in vacuo to give an oil. The oil is dissolved in dilute sodium hydroxide solution, extracted with ether to remove 1,2-dicyanomethoxybenzene and the alkali solution acidified and extracted with ether. The extract is evaporated to dryness and the residue distilled in vacuo to give 2-(2-hydroxyphenoxy)acetonitrile.

Step B. Preparation of 2-phenyl-2-(2-cyanomethoxyphenoxy)acetonitrile

A mixture of 2-(2-hydroxyphenoxy)acetonitrile (14.9 g., 0.1 mole), 2-chloro-2-phenylacetonitrile (15.2 g., 0.1 mole), finely powdered potassium carbonate (13.8 g., 0.1 mole) and 80 ml. of acetone is refluxed 3 hours. The mixture is then treated with 2-chloro-2-phenylacetonitrile (7.6 g., 0.05 mole) and potassium carbonate (6.9 g., 0.5 mole) and refluxed six hours. The mixture is filtered, the solids washed with acetone and the combined filtrate evaporated in vacuo to give an oil. Crystallization of the oil affords 2-phenyl-2-(2-cyanomethoxyphenoxy)acetonitrile.

Step C. Preparation of 2-phenyl-3-hydroxy-3-isopropylaminomethyl-3,4-dihydro-2H-1,5-benzodioxepin hydrochloride This product is prepared by the procedures described in Example 1, Steps B through F, employing the same reactants and reaction conditions there described except the 1,2-di(cyanomethoxy)benzene is replaced by an equivalent quantity of 2-phenyl-2-(2-cyanomethoxyphenoxy)acetonitrile.

Additional 2-substituted-benzodioxepins that are made by the procedures of Example 123 are identified in Table IX. These products are prepared by replacing the 2-chloro-2-phenylacetonitrile employed in Step B of Example 109 by an equivalent quantity of the halonitrile identified in the table which when worked up by the methods and conditions described in Example 123 and Steps B through F of Example 1 provide the 2-substituted-benzodioxepins identified in the following table. In some instances the acetone employed in Step F of Example 1 is replaced by another ketone or aldehyde which is identified in the table to provide the R⁵ and R⁶ substituents.

TABLE IX

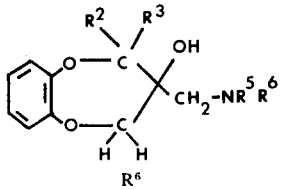 + 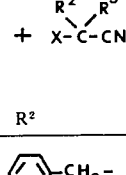 $\xrightarrow{\text{Example 97-B + Example 1, B-F}}$ 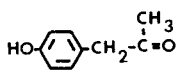

| Ex. No. | X | R² | R³ | Carbonyl Reactant | R⁶ |
|---|---|---|---|---|---|
| 124 | Br |  | H | (CH₃)₂CO | —CH(CH₃)₂ |
| 125 | Cl | CH₃ | H | 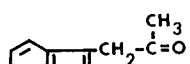 |  |
| 126 | Cl | CH₃CH₂— | H | 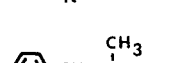 |  |
| 127 | Cl | CH₃(CH₂)₂— | H | 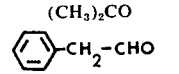 |  |
| 128 | Cl | (CH₃)₂CH— | H | (CH₃)₂CO | —CH(CH₃)₂ |
| 129 | Br | CH₃(CH₂)₃— | H | 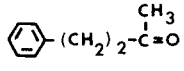 |  |
| 130 | Cl | (CH₃)₂CHCH₂— | H | 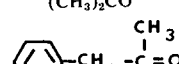 |  |
| 131 | Cl | CH₃ | CH₃ | (CH₃)₂CO | —CH(CH₃)₂ |
| 132 | Cl | CH₃ | CH₃CH₂— |  | 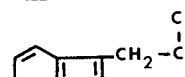 |
| 133 | Cl |  | H |  | 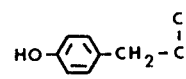 |
| 134 | Br |  | H | 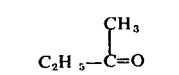 | 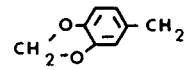 |
| 135 | Cl | CH₃ | CH₃ | C₂H₅—C(CH₃)=O | —CH(CH₃)(C₂H₅) |
| 136 | Br | CH₃(CH₂)₃— | H | 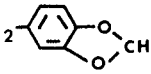 |  |
| 137 | Cl | 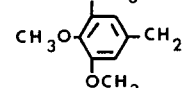 | H | CH₃—CHO | —C₂H₅ |
| 138 | Cl | CH₃ | CH₃CH₂— |  | 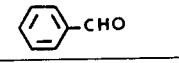 |
| 139 | Cl | CH₃CH₂ | H |  | —CH₂— |

EXAMPLE 140

2-Methyl-3-hydroxy-3-isopropylaminomethyl-7-chloro-3,4-dihydro-2H-1,5-benzodioxepin hydrochloride

Step A. Preparation of 3-chloro-6-(1-cyanoethoxy)-benzaldehyde

A mixture of 5-chlorosalicylaldehyde (78 g., 0.5 mole), finely powdered anhydrous potassium carbonate (103.5 g., 0.75 mole) and acetone (500 ml.) is stirred under reflux and 2-chloropropionitrile (33.6 g., 0.375 mole) is added over a period of about 5 minutes. The mixture is heated under reflux for 1.5 hours and then treated with potassium carbonate (34.5 g., 0.25 mole) followed by more 2-chloropropionitrile (11.2 g., 0.125 mole). Heating and stirring are continued for 3½ hours, after which the reaction mixture is filtered and the filter-cake washed with acetone. Evaporation of the combined filtrate gives 3-chloro-6-(1-cyanoethoxy)- benzaldehyde which is recrystallized from aqueous methanol.

Step B. Preparation of 3-chloro-6-(1-cyanoethoxy)-phenylformate

To a solution of 3-chloro-6-(1-cyanoethoxy)benzaldehyde (73.3 g., 0.35 mole) in acetic acid (350 ml.) is added an approximately 1M solution of peracetic acid (0.71 equivalents) in acetic acid. The reaction temperature is kept in the range 40°–45°C. by cooling. After the addition of the peracetic acid, the mixture is stirred at ambient temperature overnight. Residual peracetic acid is estimated by titrating a small aliquot, before evaporating the reaction mixture under vacuum to a small volume. Ether is added and the ethereal solution then washed with water and with 6% sodium bicarbonate solution. After a final wash with water, the ethereal solution is dried and evaporated to afford 3-chloro-6-(1-cyanoethoxy)-phenyl-formate which is purified by recrystallization from benzene petroleum ether.

Step C. Preparation of 3-chloro-6-(1-cyanoethoxy)phenol

3-Chloro-6-(1-cyanoethoxy)-phenyl-formate (56.4 g., 0.25 mole) is added to a solution of 85% potassium hydroxide (17.1 g., 0.26 mole) in 95% alcohol (200 ml.) at ambient temperature, and the mixture then stirred overnight under nitrogen. The reaction mixture is treated with a slight excess of dilute hydrochloric acid, and most of the alcohol removed under reduced pressure. The product is extracted with ether, the ethereal extract is washed with water, then with 5% sodium carbonate solution and again with water. The ethereal extract then is dried over magnesium sulfate and then over calcium sulfate and the ether removed by evaporation yielding 3-chloro-6-(1-cyanoethoxy)-phenol, which is crystallized from chloroform-petroleum ether.

Step D. Preparation of 3-chloro-6-(1-cyanoethoxy)-phenoxyacetonitrile

A mixture of 3-chloro-6-(1-cyanoethoxy)-phenol (34.6 g., 0.175 mole), finely powdered anhydrous potassium carbonate (37.2 g., 0.27 mole) and acetone (250 ml.) is stirred under reflux while chloroacetonitrile (9.8 g., 0.13 mole) is added over a period of about 5 minutes. The mixture then is heated under reflux with vigorous stirring for 1.5 hours, whereupon more potassium carbonate (12.5 g., 0.09 mole) and chloroacetonitrile (3.4 g., 0.045 mole) are added. Stirring and heating are continued for 3.5 hours, then the mixture is filtered and the filter-cake washed with acetone. Evaporation of the combined filtrate affords 3-chloro-6-(1-cyanoethoxy)-phenoxyacetonitrile which is recrystallized from aqueous alcohol.

Step E. Preparation of 2-methyl-3-hydroxy-3-isopropylaminomethyl-7-chloro-3,4-dihydro-2H-1,5-benzodioxepin hydrochloride By replacing the 1,2-di-(cyanomethoxy)benzene employed in Example 1, Step B, by an equivalent quantity of 3-chloro-6-(1-cyanoethoxy) phenoxyacetonitrile and then following the same procedures and employing the same reaction conditions described in Example 1, Steps B through F, there are obtained, sequentially
2-methyl-3-amino-4-cyano-7-chloro-2H-1,5-benzodioxepin,
2-methyl-7-chloro-3-oxo-3,4-dihydro-2H-1,5-benzodioxepin,
2-methyl-3-hydroxy-3-cyano-7-chloro-3,4-dihydro-2H-1,5-benzodioxepin,
2-methyl-3-hydroxy-3-aminomethyl-7-chloro-3,4-dihydro-2H-1,5-benzodioxepin, and
2-methyl-3-hydroxy-3-isopropylaminomethyl-7-chloro-3,4-dihydro-2H-1,5-benzodioxepin hydrochloride.

Isomers that are formed during some of the above procedures are separated from the identified compounds by known methods.

EXAMPLE 141

2-methyl-3-hydroxy-3-isopropylaminomethyl-3,4-dihydro-2H-1,5-benzodioxepin hydrochloride

Step A.—Preparation of 3-hydroxy-3-morpholino-3,4-dihydro-2H-1,5-benzodioxepin:

3-oxo-3,4-dihydro-2H-1,5-benzodioxepin (3.0 g., ca. 0.03 mole) from Steps A–C of Example 1, is dissolved in dry toluene (40 ml.). p-Toluenesulfonic acid (200 mg.) and morpholine (3.5 g., 0.04 mole) are added and an immediate exothermic reaction gives 3-hdyroxy-3-morpholine-3,4-dihydro-2H-1,5-benzodioxepin as a white precipitate, m.p. 86°–89°C.

Step B.—Preparation of 3-morpholine-2H-1,5-benzodioxepin:

The white precipitate is resuspended and stirred under reflux for about half an hour until no more water is being collected in a Dean-stark trap. Water (0.7 ml.) is obtained (theoretical 0.54 ml.). Evaporation of the solution afforded 8.2 g. (theory 6.99 g.) of 3-morpholino2H-1,5-benzodioxepin as an oil. Addition of isopropyl ether to the oil left undissolved 300 mg. of the p-toluenesulfonic acid salt of the product as a solid, m.p. 100°–104°C. Evaporation of the mother liquors yield an oil (7.3 g.) which on crystallization from a mixture of isopropyl ether/petroleum ether yielded an additional 1.6 g. of product.

The above compound can also be prepared without the use of an acidic catalyst in the following manner.

A mixture of the ketone (5.0 g., 0.03 mole), morpholine (3.0 ml, 0.033 mole) and benzene (40 ml.) are heated under reflux under nitrogen for 5 hours at which time no further water is being collected in the trap. Removal of the benzene under vacuum affords the product as an oil which crystallized on cooling and triturating.

Step C.—Preparation of 2-methyl-3-oxo-3,4-dihydro-2H-1,5-benzodioxepin:

Treatment of the 3-morpholino-2H-1,5-benzodioxepin dissolved in benzene with a slight excess of methyl iodide gives the 2-methyl-3-morpholine-3,4-dihydro-2H-1,5-benzodioxepin. Hydrolysis of this intermediate with dilute hydrochloric acid gives 2-methyl-3-oxo-3,4-dihydro-2H-1,5-benzodioxepin.

Step D.—Preparation of 2-methyl-3-hydroxy-3-isopropylaminomethyl-3,4-dihydro-2H-1,5-benzodioxepin hydrochloride:

By replacing the 3-oxo-3,4-dihydro-2H-1,5-benzodioxepin employed in Step D of Example 1 by an equivalent quantity of 2-methyl-3-oxo-3,4-dihydro-2H-1,5-benzodioxepin and following the same procedures and employing the same reagents and conditions described in Steps D through F of Example 1, there is obtained 2-methyl-3-hydroxy-3-isopropylaminomethyl-3,4-dihydro-2H-1,5-benzodioxepin hydrochloride.

EXAMPLE 142

3-Hydroxy-3-[di(2-hydroxy-2-phenylethyl)aminomethyl]-3,4-dihydro-2H-1,5-benzodioxepin hydrochloride 3-Hydroxy-3-aminomethyl-3,4-dihydro-2H-1,5-benzodioxepin (2.30 g., 11.8 millimole) and styrene oxide (1.42 g., 11.8 millimole) are dissolved in methanol (12 ml.) and the solution then is stirred at ambient temperature for 48 hours. Evaporation of the reaction mixture gives 3.64 g. of a syrup which is chromatographed on a dry silica gel (150 g.) column which had been deactivated with about 25 ml. of water and packed in a 1 3/4 inches glass column. The first three fractions obtained upon elution with a 1:1 mixture of ether and chloroform are combined and dissolved in dry ether (50 ml.) and treated with a slight excess of ethanolic hydrogen chloride. The solid material is separated and dissolved in boiling ethanol (16 ml.) clarified with charcoal and filtered. The solvent was removed from the filtrate by evaporation yielding 3-hydroxy-3-[di(2-hydroxy-2-phenylethyl)aminomethyl)-3,4-dihydro-2H-1,5-benzodioxepin hydrochloride, m.p. 221°–222° C. (dec.).

Analysis calculated for $C_{26}H_{23}NO_5.HCl$: C, 66.17; H, 6.41; Cl, 7.51; N, 2.97; Found: C, 65.76; H, 6.58; Cl, 7.77; N, 3.26.

The following examples describe alternative methods for preparing compounds of this invention.

EXAMPLE 143

3-Hydroxy-3-isopropylaminomethyl-7-nitro-3,4-dihydro-2H-1,5-benzodioxepin

Step A: Preparation of 3′-isopropyl-3,4-dihydro-2H-1,5-benzodioxepin-3-spiro-5′-oxazolidin-2′-one To a solution of phosgene (15.5 g.; 0.157 mole) in chloroform (100 ml.) cooled to 5-8° C. in a cooling bath is added a solution of 3-isopropylaminomethyl-3-hdyroxy-3,4-dihydro-2H-1,5-benzodioxepin, prepared as described in Example 1, (24.8 g.; 0.1045 mole) in chloroform (100 ml.) dropwise with stirring. The addition, which takes about 1 hour, results in the formation of a precipitate. To the suspension is added triethylamine (44.7 ml.; ca. 0.32 mole) dropwise at the same temperature. Then the reaction mixture is allowed to warm to room temperature and then stirred for 1 hour, poured into water (200 ml.) and the chloroform solution separated and washed consecutively with 10% hydrochloric acid (25 ml.), water (25 ml.), 5% sodium hydroxide solution (25 ml.) and water (2 × 25 ml.). The solution is dried over anhydrous magnesium sulphate and evaporated to a solid residue that is recrystallized from carbon tetrachloride (90 ml.) to give 20.3 g. (73.8%) of 3′-isopropyl-3,4-dihydro-2H-1,5-benzodioxepin-3-spiro-5′-oxazolidin-2′-one, m.p. 118°–120° C. Further recrystallization from di-isopropyl ether raises the m.p. to 121°–122° C.

Analysis calculated for $C_{14}H_{17}NO_4$: C, 63.86; H, 6.51; N, 5.32; Found: C, 64.08; H, 6.72; N, 5.17.

Step B: Preparation of 3′-isopropyl-7-nitro-3,4-dihydro-2H-1,5-benzodioxepin-3-spiro-5′-oxazolidin-2′-one A solution of 3′-isopropyl-3,4-dihydro-2H-1,5-benzodioxepin-3-spiro-5′-oxazolidin-2′-one (24.8 g.; 94.2 mmole) in acetic acid (100 ml.) is cooled in an ice bath to the point at which freezing begins. A mixture of 90% nitric acid and concentrated sulfuric acid (54 mls., containing 1.2 ml. of nitric acid (d 1.5) to each 10 ml. of sulfuric acid, (ca. 124 mmole) is added dropwise with stirring over a period of 20 minutes, the cooling bath then is removed and stirring continued for 2 hours. A slight rise in the temperature of the reaction mixture will be noticed (to 34° C.) and the color darkens slightly. The nitration can be followed by thin layer chromatography (TLC) on silica gel using multiple development with 1:1 carbon tetrachloride/chloroform. The reaction mixture is poured into water (400 ml.) and the crude product extracted with methylene chloride (3 × 100 ml.). After washing the extract successively with water (100 ml.), 10% sodium carbonate (75 ml.) and again with water (100 ml.), it is dried over magnesium sulphate and evaporated to a syrup. The syrup is crystallized by boiling it with ethanol (50 ml.) yielding 15.58 g. (53.8%) of 3′-isopropyl-7-nitro-3,4-dihydro-2H-1,5-benzodioxepin-3-spiro-5′-oxazolidin-2′-one, m.p. 140°–144° C. and a second crop is obtained by concentrating the mother liquor to ca. 25 ml. to give an additional 3.44 g. (11.8%) of compound, m.p. 130°–140° C.

Fractional crystallization of the first and second fractions, from ethanol (ca. 15–16 parts V/W, yields a total of 16.37 g., (56.3%) of the 7-nitro compound, m.p. 145°–147° C. pure enough for the next stages.

Analysis calculated for $C_{14}H_{16}N_2O_6$: C, 54.54; H, 5.23; N, 9.09. Found: C, 54.46; H, 5.77; N, 9.29.

Step C.—Preparation of 3-hydroxy-3-isopropylaminomethyl-7-nitro-3,4-dihydro-2H-1,5-benzodioxepin:

A mixture of 3′-isopropyl-7-nitro-3,4-dihydro-2H-1,5-benzodioxepin-3-spiro-5′-oxazolidin-2′-one (7.98 g.; 25.9 mmole), dioxane (60 ml. and 45% aqueous potassium hydroxide solution (16 ml.) in a nitrogen-filled steel pressure-vessel is heated in a rocking-furnace at 150°–160° C. for 16 hours. The reaction mixture then is poured into ether (100 ml.) and the organic layer separated. The aqueous solution is extracted with ether (100 ml.) and the combined ethereal solution is washed twice with saturated sodium chloride solution (2 × 100 ml.) and then with water (100 ml.). The ethereal solution is extracted with 2.75N hydrochloric acid (40 ml.; 0.11 mole) and twice with water (2 × 40 ml.). The combined acid and aqueous extracts is basified with 2.5N sodium hydroxide solution (70 ml.; 0.175 mole) and the liberated base extracted with ether (2 × 100 ml.). After drying the ethereal solution over anhydrous magnesium sulfate and then over calcium sulfate mixed with a little charcoal, it is evaporated to an oil that soon crystallizes providing 3-hydroxy-3-isopropylaminomethyl-7-nitro-3,4-dihydro-2H-1,5-benzodioxepin as a bright yellow solid, yield 6.33 g., (86.7%), m.p. 95–96.5' C. Recrystallization from di-isopropyl ether (63 ml.) affords 4.56 g., (62.4%) of product, m.p. 97.5°–99° C.

Analysis calculated for $C_{13}H_{18}N_2O_5$: C, 55.31; H, 6.43; N, 9.92. Found: C, 55.14; H, 6.67; N, 9.81.

EXAMPLE 144

7-amino-3-isopropylaminoemethyl-3-hydroxy-3,4-dihydro-2H-1,5-benzodioxepin

3-Isopropylaminomethyl-3-hydroxy-7-nitro-3,4-dihydro-2H-1,5-benzodioxepin prepared as described in Example 143, (1.5 g., 5.32 mmole) in ethanol (25 ml.) is hydrogenated at room temperature and a pressure of 40 p.s.i. in the presence of 5% palladium on charcoal (400 ml.). The solution then is filtered and evaporated to an oil, that crystallizes from di-isopropyl ether (15 ml.) yielding 1.11 g. (82.7%) of crude product. On recrystallization of the solid from benzene (11 ml.) with treatment with a little charcoal, there is obtained 990 mg. (73.8%) of 7-amino-3-isopropylaminomethyl-3-hydroxy-3,4-dihydro-2H-1,5-benzodioxepin, m.p. 96°–97° C.

Analysis calculated for $C_{13}H_{20}N_2O_3$: C, 61.88; H, 7.99; N, 11.10. Found: C, 61.73; H, 7.86; N, 11.29.

EXAMPLE 145

3,7-dihydroxy-3-isopropylaminomethyl-3,4-dihydro-2H-1,5-benzodioxepin

Step A.—Preparation of 7-amino-3'-isopropyl-3,4-dihydro-2H-1,5-benzodioxepin-3-spiro-5'-oxazolidin-2'-one:

A mixture of 3'-isopropyl-7-nitro-3,4-dihydro-2H-1,5-benzodioxepin-3-spiro-5'-oxazolidin-2'-one (960 mg.; 3.12 mmole), ethanol (30 ml.) and 5% palladium on charcoal (500 mg.) is shaken with hydrogen at 50 p.s.i. pressure. Hydrogen uptake is rapid and complete. After 1 hour, the catalyst is filtered off and the solvent removed in a rotary film evaporator to afford 720 mg., (88.1%) of 7-amino3'-isopropyl-3,4-dihydro-2H-1,5-benzodioxepin-3-spiro-5'-oxazolidin-2'-one, m.p. 157°–159° C. Recrystallization from ethanol (5 ml.) gives 445 mg., (51.3%) of product, m.p. 163°–164° C.

Analysis calculated for $C_{14}H_{18}N_2O_4$: C, 60.42; H, 6.52; N, 10.07; Found: C, 60.53; H, 6.66; N, 9.93.

Treatment of the 3-spiro-5'-oxazolidin-2'-one thus obtained with aqueous alkali by substantially the same method described in Example 143, Step C, provides 7-amino-3-isopropylaminomethyl-3-hydroxy-3,4-dihydro-2H-1,5-benzodioxepin.

Step B: Preparation of 7-hydroxy-3'-isopropyl-3,4-dihydro12H-1,5-benzodioxepin-3-spiro-5'-oxazolidin-2'-one A solution of 7-amino-3'-isopropyl-3,4-dihydro-2H-1,5-benzodioxepin-3-spiro-5'-oxazolidin-2'-one (3.27 g.; 11.75 mmole) in 10% sulfuric acid (65 ml.) is diazotised with 20% sodium nitrite solution (4.05 ml.; 11.75 mmole) at 0°–5° C. After stirring the mixture for 30 minutes at room temperature, excess nitrous acid is destroyed by the addition of urea using potassium iodide paper as an indicator, and the solution then is poured into a well-stirred boiling suspension of silica gel (15 g.) in 10% sulfuric acid (130 ml.) over a period of about 10 minutes. The mixture is stirred at the boiling point for about 30 minutes by which time a test for diazonium ions (using alkaline β-naphthol as an external indicator) is negative. When cool, the solids are collected, washed with a little water and dried at 60° C. in air. In order to obtain a homogeneous solid, it is boiled with ethanol for a few minutes and evaporated to dryness in a rotary film evaporator. The silica gel impregnated with crude product then is placed at the top of a column of silica gel deactivated with 15% of water, (column dimensions 18 × 1¼ ins) and development of the dry column is carried out with 1:1 ether/chloroform. The product is obtained by evaporation of the first 300 ml. of eluate, providing 1.62 g., (49.4%). The crude product is recrystallized from ethanol (20 ml.) affording a first crop of 0.93 g. (28.3%) m.p. 215.5°–217.5° C. and a second crop of 0.58 g. (17.7%) m.p. 211°–213° C. Recrystallization from ethanol provided product in the form of prisms, m.p. 216.5°–217.5° C.

Analysis calculated for $C_{14}H_{17}NO_5$: C, 60.20; H, 6.14; N, 5.02; Found: C, 59.89; H, 6.17; N, 4.80.

Step C: Preparation of 3,7-dihydroxy-3-isopropylaminomethyl-3,4-dihydro-2H-1,5-benzodioxepin A mixture of 7-hydroxy-3'-isopropyl-3,4-dihydro-2H-1,5-benzodioxepin-3-spiro-5'-oxazolidin-2'-one (200 mg.; 0.716 mmole), barium hydroxide octahydrate (1.08 g.; 3.42 mole) and water (3.2 ml.) in an evacuated sealed glass tube (a Carius tube) is heated in a rocking oven at 160°–165° C. for 16 hours. The reaction mixture then is poured into boiling water (60 ml.) with stirring and vigorous passage of carbon dioxide until all barium ions have been removed from solution (pH ca. 6.8 by narrow range paper: no precipitate when a small portion is tested with sulfate ions). The solution is filtered through a little celite and evaporated to dryness under reduced pressure, affording 187 mg. of pale brown scaly solid. The crude product is purified by dry column chromatography on silica gel deactivated with 15% of water, using 3% methanol in ether for the development. The desired product is the second component to be eluted from the column, 70.5 mg., (38.9%). After drying at 60° C. in air, the solid still contains water of crystallization and has m.p. ca. 108°–110° C. The anhydrous compound is obtained by drying the hydrate at 80° C./0.1 m.m. for 1 hour and then has m.p. 133°–134.5° C. Recrystallization from benzene (ca. 30 parts V/W) provides 3,7-dihydroxy-3-isopropylaminomethyl-3,4-dihydro-2H-1,5-benzodioxepin, m.p. 133.5°–135° C.

Analysis calculated for $C_{13}H_{19}NO_1$: C, 61.64; H, 7.56; N, 5.53; Found: C, 61.80; H, 7.20; N, 5.72.

EXAMPLE 146

3-Hydroxy-3-isopropylaminomethyl-7-methylsulfonamido-3,4-dihydro-2H-1,5-benzodioxepin

Step A: Preparation of 3'-isopropyl-7-nitro-2'-phenyl-3,4-dihydro-2H-1,5-benzodioxepin-3-spiro-5'-oxazolidine A mixture of 3-hydroxy-3-isopropylaminomethyl-7-nitro-3,4-dihydro-2H-1,5-benzodioxepin, prepared as described in Example 143, (1.41 g., 5 mmole), benzaldehyde (0.53 g.; 5 mmole), acetic acid (1 drop) and isopropanol (10 ml.) is distilled slowly: isopropanol is added at the rate required to keep the volume of the reaction mixture constant. After 3 hours, the reaction mixture is set aside at ca. 5° C. and the product that precipitates then is filtered off and recrystallized from isopropanol (ca. 20 ml.), yielding 620 mg. (33.5%) of 3'-isopropyl-7-nitro-2'-phenyl-3,4-dihydro-2H-1,5-benzodioxepin-3-spiro-5'-oxazolidine, m.p. 151°–152° C. Further recrystallization of the product from isopropanol affords the product in the form of pale yellow prisms, m.p. 152.5°–153.5° C.

Analysis calculated for $C_{20}H_{22}N_2O_5$: C, 64.85; H, 5.99; N, 7.57. Found: C, 64.98; H, 6.36; N, 7.47.

Step B: Preparation of 7-amino-3'-isopropyl-2'-phenyl-3,4-dihydro-2H-1,5-benzodioxepin-3-spiro-5'-oxazolidine:

3'-isopropyl-7-nitro-2'-phenyl-3,4-dihydro-2H-1,5-benzodioxepin-3-spiro-5'-oxazolidine (370 mg.; 1 mmole) in ethyl acetate (10 ml.) is hydrogenated at room temperature and pressure in the presence of 5% palladium on charcoal (50 mg.). When 3 moles of hydrogen has been absorbed (73 ml. at 23° C.) the catalyst is filtered off and the filtrate evaporated to a solid foam; yield 340 mg. (100%). Because of the lability of this compound, it is used in the next stage without purification.

Step C: Preparation of 3'-isopropyl-7-methansulphonamido-2'-phenyl-3,4-dihydro-2H-1,5-benzodioxepin-3-spiro-5'-oxazolidine The crude 7-amino-3'-isopropyl-2'-phenyl-3,4-dihydro-2H-1,5-benzodioxepin-3-spiro-5'-oxazolidine (352 mg.) is dissolved in dry ether (23 ml.) and 1,4-diazabicyclo[2,2,2]-octane (118 mg.; 1.065 mmole) is added. Methane sulphonyl chloride (105 mg.; 1.065 mmole) dissolved in dry ether (5 ml.) is added dropwise with stirring and the reaction mixture then is stirred at room temperature for 1 hour. The solid is filtered off and discarded: evaporation of the mother liquors affords 387.2 mg. (91%) of crude product.

Step D.—Preparation of 3-hydroxy-3-isorpopylaminomethyl-7-methanesulphonamido-3,4-dihydro-2H-1,5-benzodioxepin:

The crude 3'-isopropyl-7-methanesulphonamido-2'-phenyl-3,4-dihydro-2H-1,5-benzodioxepin-3-spiro-5'-oxazolidine (227 mg.; 0.543 mmole) is dissolved in methanol (3 ml.) and oxalic acid dihydrate (70 mg.; 0.55 mmole) is added. The mixture is stirred to effect solution of the oxalic acid and then set aside at room temperature for three hours by which time a crystalline solid separates, yielding 107.9 mg., (47.3%) of 3-hydroxy-3-isopropylaminomethyl-7-methanesulphonamido-3,4-dihydro-2H-1,5-benzodioxepin hydrogen oxalate, m.p. 207°–209°C. (dec.). Recrystallization of the product from methanol (ca. 50 parts V/W) affords pure oxalate, m.p. 214°–215°C. (dec.).

Analysis calculated for $C_{14}H_{22}N_2O_5S \cdot (COOH)_2$: C, 45.70; H, 5.75; N, 6.66; S, 7.63. Found: C, 45.08; H, 5.74; N, 6.54; S, 7.77.

By replacing the 3-spiro-5'-oxazolidine employed in Step D by an equivalent quantity of 7-amino-3'-isopropyl-2'-phenyl-3,4-dihydro-2H-1,5-benzodioxepin-3-spiro-5'-oxazolidine (Step B product) and following substantially the same procedure described in Step D, there is obtained the product of Example 144, i.e., 3-hydroxy-3-isopropylaminomethyl-7-amino-3,4-dihydro-2H-1,5-benzodioxepin.

EXAMPLE 147

7-Dimethylamino-3-isopropylaminomethyl-3-hydroxy-3,4-dihydro-2H-1,5-benzodioxepin Step A.—Preparation of 7-dimethylamino-3'-isopropyl-3,4-dihydro-2H-1,5-benzodioxepin-3-spiro-5'-oxazolidin-2'-one:

A mixture of 7-nitro-3'-isopropyl-3,4-dihydro-2H-1,5-benzodioxepin-3-spiro-5'-oxazolidin-2'-one, prepared as described in Example 143, Step B, (925 mg.; 3 mmole), ethanol (5.1 ml.), water (6.3 ml.), acetic acid (0.18 ml.), 40% aqueous formaldehyde (1.23 ml.) and 10% palladium on charcoal (200 mg.) is hydrogenated at 50 p.s.i. at room temperature until the theoretical amount of hydrogen is absorbed. The catalyst is filtered off and the filtrates are evaporated to dryness. Recrystallization of the solid residue from ethanol affords 540 mg. (58.8%) of 7-dimethylamino-3'-isopropyl-3,4-dihydro-2H-1,5-benzodioxepin-3-spiro-5'-oxazolidin-2'-one, m.p. 135°–137.5° C.

Analysis calculated for $C_{16}H_{22}N_2O_4$: C, 62.72; H, 7.24; N, 9.14; Found: C, 62.58; H, 7.22; N, 9.07.

Step B. Preparation of 7-dimethylamino-3-isopropylaminomethyl-3-hydroxy-3,4-dihydro-2H-1,5-benzodioxepin By replacing the 7-nitro-3'-isopropyl-3,4-dihydro-2H-1,5-benzodioxepin-3-spiro-5'-oxazolidin-2'-one employed in Example 143, Step C, by an equivalent quantity of 7-dimethylamino-3'-isopropyl-3,4-dihydro-2H-1,5-benzodioxepin-3-spiro-5'-oxazolidin-2'-one and following substantially the same procedure described in Example 143, Step C, there is obtained 7-dimethylamino-3-isopropylaminomethyl-3-hydroxy-3,4-dihydro-2H-1,5-benzodioxepin.

EXAMPLE 148

7-Ethoxycarboxamido-3'-isopropyl-3,4-dihydro-2H-1,5-benzodioxepin-3-spiro-5'-oxazolidin-2'-one A solution of ethyl chloroformate (342 mg.; 3.15 mmole) in chloroform (5 ml.) is added dropwise with stirring at room temperature to a mixture of 7-amino-3'-isopropyl-3,4-dihydro-2H-1,5-benzodioxepin-3-spiro-5'-oxazolidin-2'-one, prepared as described in Example 144, (556 mg.; 2 mmole) and triethylamine (333 mg.; 3.3 mmole) in chloroform (6 ml.). The reaction mixture is stirred overnight at room temperature and then is poured into water (15 ml.). The chloroform layer is separated and washed in succession with 10% hydrochloric acid (3 ml.), water (3 ml.), 10% sodium carbonate solution (3 ml.) and finally again with water (2 × 3 ml.), then is dried over magnesium sulfate and evaporated to an oil (700 mg.). Recrystallization from ethyl acetate (5 ml.) gives 562 mg. (80.3%) of product, m.p. 164°–167.5° C. On further recrystallization from the same solvent the m.p. is raised to 167°–9° C.

Analysis calculated for $C_{17}H_{22}N_2O_6$: C, 58.28; H, 6.33; N, 8.00. Found: C, 58.33; H, 6.47; N, 7.90.

EXAMPLE 149

3-Aziridinylmethyl-3-hydroxy-3,4-dihydro-2H-1,5-benzodioxepin 3,4-Dihydro-2H-1,5-benzodioxepin-3-spiro-2'-oxirane prepared as described in Example 57, Step A, (5.3 g.; 0.0298 mole) is added to a solution of ethylene imine (4.8 ml.; 0.09 mole) in methanol (60 ml.) and the mixture is stirred at room temperature for 20 hours. On evaporating the solution to dryness under reduced pressure, an orange oil (7.1 g.) is obtained, which solidifies and is recrystallized from diisopropyl ether with treatment with charcoal to yield 5.15 g. (78.2%) of 3-aziridinylmethyl-3-hydroxy-3,4-dihydro-2H-1,5-benzodioxepin, m.p. 98°–99.5° C.

EXAMPLE 150

3-(3-Hydroxy-3,4-dihydro-2H-1,5-benzodioxepin-3-ylmethyl)-2-iminothiazolidine

Solutions of concentrated hydrochloric acid (1.83 ml.) in ethanol (5 ml.) and 3-aziridinylmethyl-3-hydroxy-3,4-dihydro-2H-1,5-benzodioxepin (see Example 149) (2.4 g.; 0.011 mole) in ethanol (5 ml.) are added simultaneously to a stirred solution of sodium thiocyanate (0.81 g.; 0.01 mole) in ethanol (12.5 ml.); the rates being controlled so that the pH of the reaction mixture is kept below 4. The mixture is heated at 45°C. for 1 hour and precipitated sodium chloride is filtered off. The filtrate is evaporated to dryness and the residue shaken with a mixture of isopropanol and ether to afford 2.32 g., (68.2%) of 3-(3-hydroxy-3,4-dihydro-2H-1,5-benzodioxepin-3-ylmethyl)-2-iminothiazolidine in the form of a pink solid, m.p. 200°–203°C. to a turbid melt.

Analysis calculated for $C_{13}H_{16}N_2O_3S$ . HCl: C, 42.29; H, 5.41; Cl, 11.19; N, 8.84; S, 10.12. Found: C, 49.32; H, 5.74; Cl, 11.17; N, 8.83; S, 9.90.

EXAMPLE 151

3-tert-Butylaminomethyl-3-hydroxy-6-methoxy-3,4-dihydro-2H-1,5-benzodioxepin

Step A.—Preparation of 6-methoxy-3,4-dihydro-2H-1,5-benzodioxepin-3-spiro-2'-oxirane:

Dry dimethylsulfoxide (12 ml.) is added with stirring and cooling (water-bath at room temperature) to a mixture of sodium hydride (0.264 g.; 11 mmole) and trimethylsulfoxonium iodide (2.42 g.; 11 mmole) under dry nitrogen. The mixture is stirred for 30 minutes by which time evolution of hydrogen essentially ceases. A slurry of 6-methoxy-3-oxo-3,4-dihydro-2H-1,5-benzodioxepin (1.94 g.; 10 mmole) in dry dimethyl sulfoxide (3 ml.) is added slowly with stirring and slight cooling and the dropping funnel is rinsed through with the same solvent (2 ml.). The reaction mixture is stirred for 2 hours at room temperature and 1 hour at 50°C., then poured into water (50 ml.) and extracted with ether (3 × 15 ml.). Some ether insoluble gum is discarded. The extract is dried over magnesium sulfate and if there are signs of crystallization, methylene chloride (20 ml.) can be added before the drying agent is filtered off. Evaporation of the solution yields a semi-solid residue (834 mg.) which is slurried with methanol (2 ml.) and filtered off yielding 588 mg. (29%) of 6-methoxy-3,5-dihydro-2H-1,5-benzodioxepin-3-spiro-2'-oxirane m.p. 106°–110°C. On recrystallization of this solid from methanol (7 parts volume/weight) gives epoxide melting at 110.5°–111.5°C.

Analysis calculated for $C_{11}H_{12}O_4$: C, 63.45; H, 5.81. Found: C, 63.33; H, 5.69.

Step B.—Preparation of 3-tert-butylaminomethyl-3-hydroxy-6-methoxy-3,4-dihydro-2H-1,5-benzodioxepin:

A suspension of 6-methoxy-3,4-dihydro-2H-1,5-benzodioxepin-3-spiro-2'-oxirane (520 mg.; 2.5 mmole) in a mixture of tert-butylamine (548 mg.; 7.5 mmole) and methanol (4 ml.) is stirred at room temperature for 16 hours, by which time the solid dissolves, and reaction is complete as shown by thin layer chromatography (TLC). Evaporation of the solution yields 726 mg. of product in the form of an oil. A solution of the crude amine (698.5 mg.; 2.48 mmole) in ethyl acetate (7 ml.) is added to a hot solution of maleic acid (290 mg.; 2.5 mmole) in ethyl acetate (4 ml.). After allowing the mixture to stand for an hour at room temperature, the product is collected, washed with ethyl acetate and dried at 60°C. in air yielding 909 mg. (91.6%) of 3-tert-butylaminomethyl-3-hydroxy-6-methoxy-3,4-dihydro-2H-1,5-benzodioxepin hydrogen maleate, m.p. 188°–190.5°C. (dec.) after softening at ca. 184° C. Recrystallization from ethanol (16 ml.) provides 686 mg. (69.1%) of product, m.p. 193°–195° C. (dec.).

Analysis calculated for $C_{15}H_{23}NO_4$ . $C_4H_4O_4$: C, 57.42; H, 6.85; N, 3.52. Found: C, 57.37; H, 6.82; N, 3.80.

EXAMPLE 152

3,6-Dihydroxy-3-isopropylaminomethyl-3,4-dihydro-2H-1,5-benzodioxepin hydrobromide 3-Hydroxy-3-isopropylaminomethyl-6-methoxy-3,4-dihydro-2H-1,5-benzodioxepin, prepared as described in Example 22, (600 mg.) is dissolved in 10 ml. of 48% hydrobromic acid and refluxed for 10 hours. The resulting yellow-red solution is evaporated to dryness in vacuo, the residue dissolved in ethanol, warmed with charcoal and filtered. The filtrate is evaporated to dryness to give a foamy semi-solid. The semi-solid is triturated with ethyl acetate to give 596 mg. of crystalline 3,6-dihydroxy-3-isopropylaminomethyl-3,4-dihydro-2H-1,5-benzodioxepin hydrobromide, m.p. 193°–195° C. Recrystallization several times from a mixture of methanolethyl acetate raises the melting point to 196°–197° C. (with gassing).

Analysis calculated for $C_{13}H_{19}NO_4$ .HBr: C, 46.72; H, 6.03; N, 4.19; Br, 23.91. Found: C, 47.00; H, 6.39; N, 4.05; Br, 24.02.

EXAMPLE 153

3-Guanidinomethyl-3-hydroxy-3,4-dihydro-2H-1,5-benzodioxepin . $H_2SO_4$

A mixture of 3-aminomethyl-3-hydroxy-3,4-dihydro-2H-1,5-benzodioxepin, prepared as described in Example 1, Step E, (2.02 g.; 10.35 mmole), S-methylisothiouronium sulfate (2.88 g.; 10.35 mmole), dimethylformamide (15 ml.) and water (2 ml.) is heated at 90°–100° C. for 5 hours. The mixture is allowed to cool to room temperature and unreacted methylisothiouronium sulfate is filtered off. Evaporation of the solution to dryness and recrystallization of the residue from an aqueous acetone/ethanol mixture yields 0.73 g. (24.6%) of 3-guanidinomethyl-3-hydroxy-3,4-dihydro-2H-1,5-benzodioxepin . $H_2SO_4$, m.p. 245°–247° C. (dec.).

Analysis calculated for $(C_{11}H_{15}N_3O_3)_2$ . $H_2SO_4$: C, 46.15; H, 6.11; N, 14.68; Found: C, 46.40; H, 6.04; N, 15.20.

EXAMPLE 154

3-Hydroxy-3-(3-phenylguanidinomethyl)-3,4-dihydro-2H-1,5-benzodioxepin

A mixture of 3-aminomethyl-3-hydroxy-3,4-dihydro-2H-1,5-benzodioxepin (1.95 g.; 10 mmole), S-methyl-N-phenylisothiouronium iodide (2.94 g.; 10 mmole) and ethanol (20 ml.) is heated under reflux for 12 hours. Evaporation of the solution affords a pale yellow oil, that on alkaline work-up yields 3-hydroxy-3-(3-phenylguanidinomethyl)-3,4-dihydro-2H-1,5-benzodioxepin, m.p. 184°–187° C. (from 1,2-dimethoxyethane).

Analysis calculated for $C_{17}H_{19}N_3O_3$: C, 65.16; H, 6.11; N, 13.41; Found: C, 64.87; H, 6.41; N, 13.55.

The invention further provides pharmaceutical compositions comprising, as active ingredient, at least one of the compounds according to the invention in association with a pharmaceutical carrier or excipient. The compounds may be presented in a form suitable for sublingual, oral, rectal, topical, or parenteral administration. Thus, for example, compositions for oral administration can be solid or liquid and can take the form of capsules, tablets, coated tablets, suspensions, solutions, etc., such compositions comprising carriers or excipients conventionally used in the pharmaceutical art. Thus suitable tabletting or encapsulating excipients include lactose, potato and maize starches, talc, dicalcium phosphate, stearic acid, magnesium stearate, powdered cellulose, or other known innocuous substances.

Compositions for sublingual administration can take the form of soluble tablets.

Liquid compositions can be in the form of aqueous solutions or suspensions together with suitable flavoring and coloring ingredients conventionally used in the pharmaceutical art.

For parenteral administration, the carrier or excipient can be a sterile, parenterally acceptable liquid, e.g., pyrogen free water, or a parenterally acceptable oil, e.g., arachis oil.

In compositions for rectal administration, the carrier can comprise a suppository base, e.g., cocoa butter, a glyceride, or a polyethylene glycol or mixtures thereof.

For topical use the drug can be administered in the form of a spray of a suitable solution or suspension.

Advantageously, the compositions can be formulated as dosage units, each unit being adapted to supply a fixed dose of active ingredient. Sublingual tablets, oral tablets, coated tablets, capsules, ampoules, suppositories and pressurized sprays are examples of preferred dosage unit forms according to the invention. Each dosage unit adapted for sublingual or oral administration can conveniently contain 1 to 20 mg., and preferably 2 to 10 mg., of the active ingredient; each dosage unit adapted for parenteral administration can conveniently contain 0.1 to 5 mg., and preferably 0.1 to 1.0 mg. of the active ingredient; the pressurized spray can conveniently contain 2 to 20 mg. per ml. of the active ingredient in a dispersing unit which will deliver a controlled dosage of 0.05 to 0.5 mg.

In the following examples, pharmaceutical compositions according to the invention are illustrated, other acid addition salts, or other active compounds can be substituted for that named, as desired.

The pharmaceutical compositions of the following examples contain 3-hydroxy-3-isopropylaminomethyl-3,4-dihydro-2H-1,5-benzodioxepin hydrochloride as active ingredient.

EXAMPLE 155

A sublingual tablet is prepared by conventional methods containing

|  | Mg. |
|---|---|
| Active compound | 5 |
| Lactose, U.S.P. | 110 |
| Gum acacia | 13 |
| Magnesium stearate | 2 |

EXAMPLE 156

Capsules are prepared by conventional methods containing per capsule

|  | Mg. |
|---|---|
| Active compound | 5 |
| Magnesium stearate | 2 |
| Lactose, U.S.P. | 193 |

EXAMPLE 157

An injectable solution is prepared by conventional methods containing per unit dosage

|  | Mg. |
|---|---|
| Active compound | 1 |
| Sodium chloride | 9 |
| Distilled water, q.s. to | 1.0 |

While the invention has been illustrated by certain specific members of the novel 3,3-disubstitutedbenzodioxepins, made by certain specific methods and formulated into certain specific dosage forms, it is to be understood that the invention is not to be considered limited by or to the specific embodiments illustrated but is to encompass other members of the novel products falling within the scope of the generic disclosure and claims as well as other methods or modifications of the methods described for their preparation as well as other formulations, all of which would be obvious in view of the teaching herein to one skilled in the art.

What is claimed is:

1. A 3,3-disubstituted-benzodioxepin having the structure

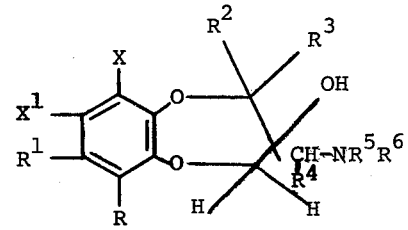

and acid addition salts thereof wherein

R is selected from hydrogen, hydroxy, lower alkyl and lower alkoxy;

$R^1$ is selected from hydrogen, chloro, bromo, lower alkyl, nitro, amino, $C_{1-3}$ alkylsulfonylamino, $C_{1-3}$ alkoxycarbonylamino, lower carbalkoxyamino, hydroxy and lower alkoxy;

X and $X^1$ are selected from hydrogen, lower alkyl and halogen;

$R^2$ is selected from hydrogen, lower alkyl, phenyl, phenyl-lower alkyl and lower cycloalkyl;

$R^3$ is selected from hydrogen, lower alkyl, phenyl and phenyl-lower alkyl;

$R^4$ is selected from hydrogen and lower alkyl;

$R^5$ is selected from hydrogen, lower alkyl, and 2-phenyl-2-hydroxyethyl;

$R^6$ is hydroxyalkyl of a maximum of 4 carbon atoms substituted with ω-(1,2,5-thiadiazolyloxy).

2. A 3,3-disubstituted-benzodioxepin as claimed in claim 1 wherein $R, R^1, X, X^1, R^2, R^3$ and $R^5$ each represent hydrogen. $R^4$ represents lower alkyl and $R^6$ has the meaning assigned in claim 1.

3. A 3,3-disubstituted-benzodioxepin as claimed in claim 1 wherein $R, R^1, X, X^1, R^2, R^3, R^4$, and $R^5$ each represent hydrogen and $R^6$ has the meaning assigned in claim 1.

4. A 3,3-disubstituted-benzodioxepin as claimed in claim 1 wherein $R, R^1, X, X^1, R^3$ and $R^5$ each represent hydrogen and $R^2, R^4$ and $R^6$ have the meaning assigned to each in claim 1.

5. A product as claimed in claim 3, wherein $R^6$ is 3-(1,2,5-thiadiazolyloxy)-2-hydroxypropyl.

* * * * *